United States Patent
White

(10) Patent No.: US 11,433,074 B2
(45) Date of Patent: *Sep. 6, 2022

(54) METHODS OF TREATING GLIOBLASTOMA

(71) Applicant: TRIACT THERAPEUTICS, INC., San Francisco, CA (US)

(72) Inventor: Thomas F. White, San Francisco, CA (US)

(73) Assignee: TRIACT THERAPEUTICS, INC., San Francisco, CA (US)

( * ) Notice: Subject to any disclaimer, the term of this patent is extended or adjusted under 35 U.S.C. 154(b) by 171 days.

This patent is subject to a terminal disclaimer.

(21) Appl. No.: 16/626,282

(22) PCT Filed: Jun. 22, 2018

(86) PCT No.: PCT/US2018/039103
§ 371 (c)(1),
(2) Date: Dec. 23, 2019

(87) PCT Pub. No.: WO2018/237327
PCT Pub. Date: Dec. 27, 2018

(65) Prior Publication Data
US 2020/0113909 A1    Apr. 16, 2020

Related U.S. Application Data

(60) Provisional application No. 62/523,689, filed on Jun. 22, 2017.

(51) Int. Cl.
*A61K 31/522* (2006.01)
*A61K 35/00* (2006.01)
*A61K 45/06* (2006.01)
*C12Q 1/6886* (2018.01)
*C12Q 1/6827* (2018.01)
*A61P 35/00* (2006.01)

(52) U.S. Cl.
CPC ............ *A61K 31/522* (2013.01); *A61P 35/00* (2018.01); *C12Q 1/6827* (2013.01); *C12Q 1/6886* (2013.01); *A61K 45/06* (2013.01)

(58) Field of Classification Search
CPC ...... A61K 31/522; A61K 35/00; A61K 45/06; C12Q 1/6886; C12Q 1/6827; C12Q 2600/106; C12Q 2600/154
See application file for complete search history.

(56) References Cited

U.S. PATENT DOCUMENTS

| | | | |
|---|---|---|---|
| 5,262,564 A | 11/1993 | Kun et al. | |
| 5,464,871 A | 11/1995 | Kun et al. | |
| 5,473,074 A | 12/1995 | Kun et al. | |
| 5,482,975 A | 1/1996 | Kun et al. | |
| 5,484,951 A | 1/1996 | Kun et al. | |
| 5,516,941 A | 5/1996 | Kun et al. | |
| 5,519,053 A | 5/1996 | Kun et al. | |
| 5,583,155 A | 12/1996 | Kun et al. | |
| 5,652,260 A | 7/1997 | Kun et al. | |
| 5,652,367 A | 7/1997 | Kun et al. | |
| 5,670,518 A | 9/1997 | Kun et al. | |
| 5,736,576 A | 4/1998 | Kun et al. | |
| 5,753,674 A | 5/1998 | Kun et al. | |
| 5,783,599 A | 7/1998 | Kun et al. | |
| 5,877,185 A | 3/1999 | Kun et al. | |
| 5,908,861 A | 6/1999 | Kun | |
| 5,922,775 A | 7/1999 | Kun et al. | |
| 6,004,978 A | 12/1999 | Kun et al. | |
| 6,017,958 A | 1/2000 | Kun et al. | |
| 6,169,104 B1 | 1/2001 | Tuse et al. | |
| 6,303,621 B1 | 10/2001 | Kun | |
| 6,303,629 B1 | 10/2001 | Kun | |
| 6,316,495 B1 | 11/2001 | Kun et al. | |
| 6,326,402 B1 | 12/2001 | Kun et al. | |
| 7,179,484 B2 | 2/2007 | Singh | |
| 7,405,227 B2 | 7/2008 | Kun et al. | |
| 7,538,252 B2 | 5/2009 | Ossovskaya et al. | |
| 7,732,491 B2 | 6/2010 | Sherman et al. | |
| 7,994,222 B2 | 8/2011 | Ossovskaya et al. | |
| 8,143,447 B2 | 3/2012 | Moore et al. | |
| 8,377,985 B2 | 2/2013 | Kun et al. | |
| 8,507,000 B2 | 8/2013 | Mulye | |
| 2006/0088840 A1 | 4/2006 | Giesing et al. | |
| 2007/0015814 A1 | 1/2007 | Kun et al. | |
| 2007/0036859 A1 | 2/2007 | Perry et al. | |
| 2007/0292883 A1 | 12/2007 | Ossovskaya et al. | |

(Continued)

FOREIGN PATENT DOCUMENTS

| WO | WO-9104663 A1 | 4/1991 |
|---|---|---|
| WO | WO-9206687 A1 | 4/1992 |

(Continued)

OTHER PUBLICATIONS

Blakeley et al. Phase I study of iniparib concurrent with monthly or continuous temozolomide dosing schedules in patients with newly diagnosed malignant gliomas. J Neurooncol 125(1):123-131 (2015).
Co-pending U.S. Appl. No. 16/626,288, filed Dec. 23, 2019.
Domingo-Musibay et al. What next for newly diagnosed glioblastoma? Future Oncol. 11(24):3273-3283 (2015).
International Application No. PCT/US2018/039126 International Search Report and Written Opinion dated Nov. 26, 2018.
Lincoln, DT et al.: Thioredoxin and Thioredoxin Reductase Expression in Thyroid Cancer Depends on Tumour Aggressiveness. Anticancer Research. vol. 30, No. 3, 767-776 (2010).
Llombart-Cussac et al.: SOLTI NeoPARP: a phase II randomized study of two schedules of iniparib plus paclitaxel versus paclitaxel alone as neoadjuvant therapy in patients with triplenegative breast cancer. Breast Cancer Research and Treatment. vol. 154, No. 2, 351-357 (2015).
Nabors et al. A Safety Run-In and Randomized Phase 2 Study of Cilengitide Combined With Chemoradiation for Newly Diagnosed Glioblastoma (NABTT 0306). Cancer 118(22):5601-5607 (2012).

(Continued)

*Primary Examiner* — Sun Jae Yoo
(74) *Attorney, Agent, or Firm* — Wilson Sonsini Goodrich & Rosati

(57) ABSTRACT

Disclosed herein are methods and compounds for treating glioblastoma with iniparib. Also disclosed herein is a method of selecting subjects having a glioblastoma for treatment based on a biomarker panel.

13 Claims, 5 Drawing Sheets

(56) References Cited

U.S. PATENT DOCUMENTS

| | | |
|---|---|---|
| 2008/0076778 A1 | 3/2008 | Ossovskaya et al. |
| 2008/0176946 A1 | 7/2008 | Ossovskaya et al. |
| 2008/0262062 A1 | 10/2008 | Ossovskaya et al. |
| 2009/0048344 A1 | 2/2009 | Forenzo et al. |
| 2009/0076122 A1 | 3/2009 | Kun et al. |
| 2009/0123419 A1 | 5/2009 | Sherman et al. |
| 2009/0149397 A1 | 6/2009 | Ossovskaya et al. |
| 2009/0149417 A1 | 6/2009 | Ossovskaya et al. |
| 2009/0275608 A1 | 11/2009 | Ossovskaya et al. |
| 2009/0291924 A1 | 11/2009 | Ossovskaya et al. |
| 2010/0003192 A1 | 1/2010 | Sherman et al. |
| 2010/0160442 A1 | 6/2010 | Ossovskaya et al. |
| 2010/0279327 A1 | 11/2010 | Ossovskaya et al. |
| 2012/0004260 A1 | 1/2012 | Ossovskaya et al. |
| 2012/0130144 A1 | 5/2012 | Sherman et al. |
| 2012/0238601 A1 | 9/2012 | Moore et al. |
| 2012/0269861 A1 | 10/2012 | Sherman et al. |
| 2013/0274281 A1 | 10/2013 | Bradley |
| 2013/0331457 A1 | 12/2013 | Kun et al. |
| 2014/0044788 A1 | 2/2014 | Verma et al. |
| 2016/0032368 A1 | 2/2016 | Vlassenbroeck et al. |
| 2017/0112809 A1 | 4/2017 | Orwar et al. |
| 2021/0137929 A1* | 5/2021 | White .................. C12Q 1/6886 |

FOREIGN PATENT DOCUMENTS

| | | | |
|---|---|---|---|
| WO | WO-9218123 A2 | 10/1992 | |
| WO | WO-9307868 A1 | 4/1993 | |
| WO | WO-9409776 A1 | 5/1994 | |
| WO | WO-9426730 A2 | 11/1994 | |
| WO | WO-9622791 A1 | 8/1996 | |
| WO | WO-9746228 A1 | 12/1997 | |
| WO | WO-9842328 A1 | 10/1998 | |
| WO | WO-9851307 A1 | 11/1998 | |
| WO | WO-9851308 A1 | 11/1998 | |
| WO | WO-9920263 A1 | 4/1999 | |
| WO | WO-0009114 A1 | 2/2000 | |
| WO | WO-2006135873 A2 | 12/2006 | |
| WO | WO-2007011962 A2 | 1/2007 | |
| WO | WO-2008030883 A2 | 3/2008 | |
| WO | WO-2008030887 A2 | 3/2008 | |
| WO | WO-2008030891 A2 | 3/2008 | |
| WO | WO-2008030892 A2 | 3/2008 | |
| WO | WO-2008089272 A1 | 7/2008 | |
| WO | WO-2008147418 A1 | 12/2008 | |
| WO | WO-2009050738 A2 | 4/2009 | |
| WO | WO-2009051815 A1 | 4/2009 | |
| WO | WO-2009064444 A2 | 5/2009 | |
| WO | WO-2009064738 A2 | 5/2009 | |
| WO | WO-2009073869 A1 | 6/2009 | |
| WO | WO-2009100159 A2 | 8/2009 | |
| WO | WO-2018237327 A1 | 12/2018 | |
| WO | WO-2018237344 A1 | 12/2018 | |
| WO | WO-2019067991 A1 | 4/2019 | |

OTHER PUBLICATIONS

O'shaugnessy et al.: Iniparib plus Chemotherapy in Metastatic Triple-Negative Breast Cancer. The New England Journal of Medicine. vol. 365, No. 3, 205-214 (2011).

PCT/US2018/039103 International Search Report and Written Opinion dated Sep. 19, 2018.

PCT/US2018/053558 International Search Report and Written Opinion dated Dec. 4, 2018.

Saba et al., A comparative oncology study of iniparib defines its pharmacokinetic profile and biological activity in a naturally-occurring canine cancer model. PLoS One 11(2):e0149194 (2016).

Ayhan et al.: Neoadjuvant Chemotherapy in Gynecological Cancers. Eur J Gynaecol Oncol. 27(1): 11-15 (2006).

Ayhan et al.: Topotecan as a Second-Line Therapy in Patients With Ovarian and Primary Peritoneal Cancer: Initial Response and Long-Term Follow-Up. Eur J Gynaecol Oncol. 27(6): 603-606 (2006).

Berge et al. Pharmaceutical Salts. Journal of Pharmaceutical Sciences 66(1):1-19 (Jan. 1977).

Bundgaard. Design and Application of Prodrugs. Textbook of Drug Design and Development. Krosgaard-Larsen and Bundgaard. Chapter 5. pp. 113-191 (1991).

Bundgaard. Design of Prodrugs. Elsevier, 1985.

Bundgaard. Means to Enhance Penetration: Prodrugs as a Means to Improve the Delivery of Peptide Drugs. Advanced Drug Delivery Review 8:1-38 (1992).

Chen et al.: Potential for Selective Modulation of Glutathione in Cancer Chemotherapy. Chem Biol Interact 111-112: 263-275 (1998).

Co-pending U.S. Appl. No. 16/652,387, filed Mar. 30, 2020.

Khalid, et al. Long Circulating Poly(Ethylene Glycol)-Decorated Lipid Nanocapsules Deliver Docetaxel to Solid Tumors. Pharmaceutical Research. 2006;23(4):752-758.

Mendeleyev et al.: Potential Chemotherapeutic Activity of 4-iodo-3-nitrobenzamide. Metabolic Reduction to the 3-nitroso Derivative and Induction of Cell Death in Tumor Cells in Culture. Biochem Pharmacol 50(5): 705-714 (1995).

Rice et al.: Induction of endonuclease-mediated apoptosis in tumor cells by C-nitroso-substituted ligands of poly(ADP-ribose) polymerase. Proc. Natl. Acad. Sci. USA 89: 7703-7707 (1992).

Widder et al. Section III: Prodrugs Kinetics. Method in Enzymology. 112:309-396 (1985).

* cited by examiner

METHODS OF TREATING GLIOBLASTOMA

CROSS-REFERENCE

This application is a US National Phase of International Application No. PCT/US2018/039103, filed on Jun. 22, 2018, which claims the benefit of U.S. Provisional Application No. 62/523,689, filed on Jun. 22, 2017, each of which is incorporated herein by reference in its entirety.

BACKGROUND OF THE DISCLOSURE

Cancer can develop in any tissue or organ at any age. The etiology of cancer may not be clearly defined at times; however, mechanisms such as genetic susceptibility, chromosome breakage disorders, viruses, environmental factors and immunologic disorders have all been linked to a malignant cell growth and transformation.

Worldwide, more than 10 million people are diagnosed with cancer every year and it is estimated that this number will grow to about 15 million new cases every year by 2020. Cancer causes six million deaths every year or about 12% of the deaths worldwide.

SUMMARY OF THE DISCLOSURE

Disclosed herein, in certain embodiments, are methods of treating a subject having glioblastoma. In some embodiments, also disclosed herein are methods of selecting subjects having a glioblastoma for treatment based on a biomarker panel described herein. In additional embodiments, described herein are methods of monitoring the treatment progress based on the expression level of biomarkers from the biomarker panel described herein.

Disclosed herein, in certain embodiments, is a method of selecting a subject having glioblastoma or suspected of having glioblastoma for treatment, the method comprising: (a) processing an extracted genomic DNA with a deaminating agent to generate a genomic DNA sample comprising deaminated nucleotides, wherein the extracted genomic DNA is obtained from a biological sample from the subject having glioblastoma or suspected of having glioblastoma; (b) generating a methylation profile comprising the gene MGMT; (c) determining whether the subject has an MGMT promoter methylation; and (d) selecting subjects with an MGMT promoter methylation for treatment with about 2 mg/kg to about 10 mg/kg of 4-iodo-3-nitrobenzamide or a salt, metabolite or prodrug thereof; about 0 mg/m² to about 90 mg/m² of temozolomide; and radiation. In some embodiments, disclosed herein is a method of treating a subject having glioblastoma characterized with an MGMT promoter methylation, comprising administering to the subject about 2 mg/kg to about 10 mg/kg of 4-iodo-3-nitrobenzamide or a salt, metabolite or prodrug thereof; about 0 mg/m² to about 90 mg/m² of temozolomide; and radiation, thereby treating the subject having glioblastoma characterized with an MGMT promoter methylation, wherein the subject is determined to have the MGMT promoter methylation by a) processing an extracted genomic DNA with a deaminating agent to generate a genomic DNA sample comprising deaminated nucleotides, wherein the extracted genomic DNA is obtained from a biological sample from the subject having glioblastoma or suspected of having glioblastoma; b) generating a methylation profile comprising the gene MGMT; and determining whether the subject has an MGMT promoter methylation. In some embodiments, disclosed herein is a method of treating a subject with a treatment regimen comprising 4-iodo-3-nitrobenzamide or a salt, metabolite or prodrug thereof, wherein the subject is suffering from glioblastoma, the method comprising: determining whether the subject has an MGMT promoter methylation comprising: obtaining or having obtained a biological sample from the subject; and performing or having performed a methylation assay on the biological sample to determine if the subject has the MGMT promoter methylation; and if the subject has an MGMT promoter methylation, then administering the treatment regimen comprising 4-iodo-3-nitrobenzamide or a salt, metabolite or prodrug thereof to the subject, and if the subject does not have an MGMT promoter methylation, then administering a first-line treatment for glioblastoma to the subject, wherein a medium overall survival for the subject having an MGMT promoter methylation is extended following administration of the treatment regimen comprising 4-iodo-3-nitrobenzamide or a salt, metabolite or prodrug thereof than it would be if the first-line treatment were administered; wherein the treatment regimen comprising 4-iodo-3-nitrobenzamide or a salt, metabolite or prodrug thereof comprises: about 2 mg/kg to about 10 mg/kg of 4-iodo-3-nitrobenzamide or a salt, metabolite or prodrug thereof; about 0 mg/m² to about 90 mg/m² of temozolomide; and radiation. In some embodiments, the methylation profile further comprises the methylation status of TP53, PTEN, or a combination thereof. In some embodiments, about 6 mg/kg to about 9 mg/kg of 4-iodo-3-nitrobenzamide or a salt, metabolite or prodrug thereof is administered to the subject. In some embodiments, about 7 mg/kg to about 8.6 mg/kg of 4-iodo-3-nitrobenzamide or a salt, metabolite or prodrug thereof is administered to the subject. In some embodiments, about 8 mg/kg to about 8.6 mg/kg of 4-iodo-3-nitrobenzamide or a salt, metabolite or prodrug thereof is administered to the subject. In some embodiments, about 8 mg/kg of 4-iodo-3-nitrobenzamide or a salt, metabolite or prodrug thereof is administered to the subject. In some embodiments, the 4-iodo-3-nitrobenzamide or a salt, metabolite or prodrug thereof is administered to the subject once per day. In some embodiments, the 4-iodo-3-nitrobenzamide or a salt, metabolite or prodrug thereof is administered to the subject for about twice a week. In some embodiments, the 4-iodo-3-nitrobenzamide or a salt, metabolite or prodrug thereof is administered to the subject for about four, five or six weeks. In some embodiments, the 4-iodo-3-nitrobenzamide or a salt, metabolite or prodrug thereof is administered to the subject for about six weeks. In some embodiments, about 70 mg/m² to about 80 mg/m² of temozolomide is administered to the subject. In some embodiments, about 75 mg/m² of temozolomide is administered to the subject. In some embodiments, about 0 mg/m² to about 70 mg/m² of temozolomide is administered to the subject. In some embodiments, about 5 mg/m² of temozolomide is administered to the subject. In some embodiments, about 10 mg/m² of temozolomide is administered to the subject. In some embodiments, about 15 mg/m² of temozolomide is administered to the subject. In some embodiments, about 20 mg/m² of temozolomide is administered to the subject. In some embodiments, temozolomide is not administered to the subject. In some embodiments, temozolomide is administered to the subject daily. In some embodiments, temozolomide is administered to the subject for about four, five or six weeks. In some embodiments, temozolomide is administered to the subject for about six weeks. In some embodiments, about 60 Gy of radiation is administered to the subject over the course of about four, five, or six weeks. In some embodiments, about 60 Gy of radiation is administered to the subject over the course of about six weeks. In some embodiments, upon completion of about six weeks of treatment with a combination of 4-iodo-3-nitrobenzamide or a salt, metabolite or prodrug thereof, temozolomide and radiation, the subject receives a treatment break of about four weeks. In some embodiments, the method further comprises a maintenance regimen. In some embodiments, the maintenance regimen comprises about 8.6 mg/kg of 4-iodo-3-nitrobenzamide or a salt, metabolite or prodrug thereof, and about 150 mg/m² to about 200 mg/m² of temozolomide. In some embodiments, the 4-iodo-3-nitrobenzamide or a salt, metabolite or prodrug thereof is administered to the subject once per day. In some embodiments, the 4-iodo-3-nitrobenzamide or a salt, metabolite or prodrug thereof is administered to the subject for about twice a week. In some embodiments, the 4-iodo-3-nitrobenzamide or a salt, metabolite or prodrug thereof is administered to the subject for about 1-6 cycles. In some embodiments, the temozolomide is administered to the subject on Days 1-5 of each cycle. In some embodiments, the temozolomide is administered to the subject for about 1-6 cycles. In some embodiments, each cycle comprises about 28 days. In some embodiments, the 4-iodo-3-nitrobenzamide or a metabolite thereof is formulated for parenteral administration. In some embodiments, the parenteral administration comprises intravenous, intra-arterial, intracranial, intracerebral, intracerebroventricular, or intrathecal administration. In some embodiments, the 4-iodo-3-nitrobenzamide or a salt, metabolite or prodrug thereof is formulated as an injection. In some embodiments, the 4-iodo-3-nitrobenzamide or a salt, metabolite or prodrug thereof is formulated as an infusion. In some embodiments, the glioblastoma is a primary glioblastoma. In some embodiments, the glioblastoma is a secondary tumor. In some embodiments, the subject has a grade III or grade IV glioblastoma. In some embodiments, the combination of 4-iodo-3-nitrobenzamide or a metabolite thereof, radiation, and optionally temozolomide extends the median overall survival. In some embodiments, the median overall survival is extended to about 16 to about 24 months. In some embodiments, the median overall survival is extended to about 21 months. In some embodiments, the combination of 4-iodo-3-nitrobenzamide or a metabolite thereof, radiation, and optionally temozolomide reduces the hazard rate of death. In some embodiments, the hazard rate of death is reduced from about 0.6 to about 0.42.

Disclosed herein, in certain embodiments, is a method of treating glioblastoma in a subject in need thereof, comprising administering to the subject: about 8 mg/kg of 4-iodo-3-nitrobenzamide or a salt, metabolite or prodrug thereof; about 75 mg/m² of temozolomide; and radiation.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1:
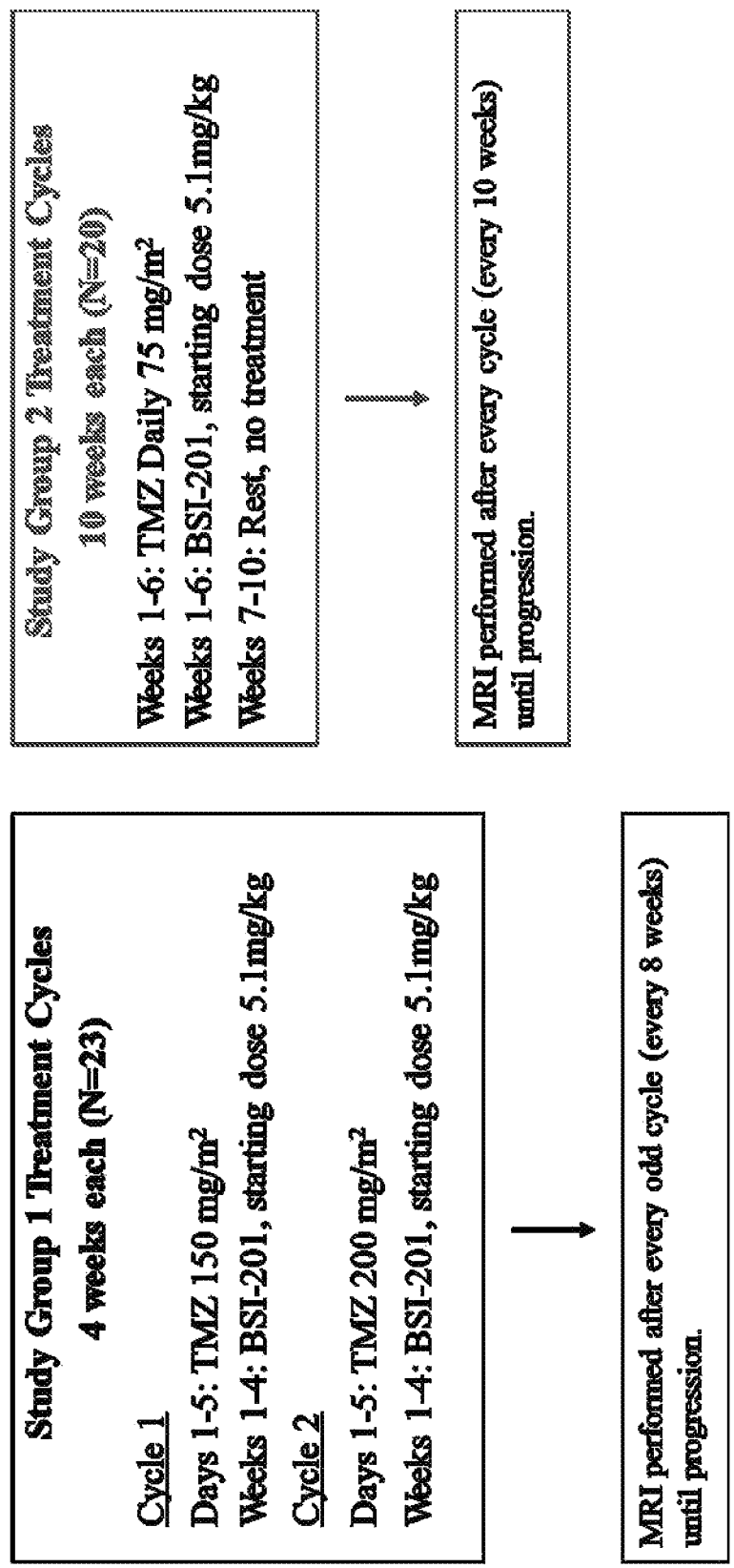
FIG. 1 illustrates an exemplary Phase I treatment schema.

Glioblastomas, or glioblastoma multiforme (GBM), are tumors that arise from astrocytes or the star-shaped cells that make up the "glue-like," or supportive tissue of the brain. Glioblastoma is fast-growing, and in some cases, it is the most common primary tumor of the central nervous system in adults. In some cases, glioblastoma is further classified into primary glioblastoma (or de novo glioblastoma) or secondary tumor. In additional cases, glioblastoma is divided into grade I, grade II, grade III and grade IV glioblastoma.

Glioblastoma is considered one of the more difficult cancers to treat, due to the heterogeneity at the cellular, molecular, biological and genetic levels. For example, glioblastomas are characterized by extent of infiltration into the brain parenchyma, marked angiogenesis, intrinsic resistance to apoptosis and genomic instability (Furnari, et al., "Malignant astrocytic glioma: genetics, biology, and paths to treatment." Genes Dev (2007) 21: 2683-2710). Furthermore, due to the tumor make-up comprising a diverse array of different cell types, and the presence of heterogeneity at both transcriptional and genomic levels, resistance to treatment and recurrence are elevated as compared to other cancers. Khosla, D. "Concurrent therapy to enhance radiotherapeutic outcomes in glioblastoma," Ann Transl Med (2016) 4(3): 54.

In some instances, treatments for glioblastoma comprise surgery, chemotherapy, radiation, or a combination thereof. In some cases, targeted therapy such as PDZ1i (113B7) which inhibits MDA09/Syntenin activity, rindopepimut (Celldex), and DCVax® (Northwest Biotherapeutics) are also contemplated.

In some embodiments, described herein is a method for treating glioblastoma with a nitrobenzamide compound. In some embodiments, the nitrobenzamide compound is encompassed by Formula (I):

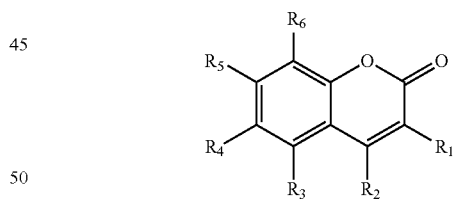

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or prodrugs thereof. $R_1$, $R_2$, $R_3$, $R_4$, and $R_5$ can also be a halide such as chloro, fluoro, or bromo.

In some embodiments, the nitrobenzamide compound is 4-iodo-3-nitrobenzamide (also known as iniparib and BSI201). In some instances, 4-iodo-3-nitrobenzamide has the structure

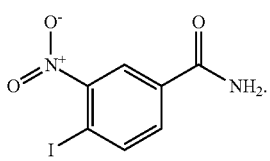 [SMILES: NC(=O)c1ccc(I)c([N+](=O)[O-])c1]

In some embodiments, the nitrobenzamide compound is a compound described in U.S. Pat. No. 5,464,871.

In some embodiments, disclosed herein is a method of treating glioblastoma with a combination of a nitrobenzamide compound described supra, temozolomide, and radiation. In some instances, the nitrobenzamide compound is a compound encompassed by Formula (I). In some instances, the nitrobenzamide compound is 4-iodo-3-nitrobenzamide or a salt, metabolite or prodrug thereof.

In some embodiments, also disclosed herein is a method of treating glioblastoma in a subject in need thereof, comprising administering to the subject: about 8 mg/kg of 4-iodo-3-nitrobenzamide or a salt, metabolite or prodrug thereof; about 75 mg/m$^2$ of temozolomide; and radiation.

In some embodiments, additionally disclosed herein is a method of selecting a subject having glioblastoma or suspected of having glioblastoma for treatment, the method comprising: (a) processing an extracted genomic DNA with a deaminating agent to generate a genomic DNA sample comprising deaminated nucleotides, wherein the extracted genomic DNA is obtained from a biological sample from the subject having glioblastoma or suspected of having glioblastoma; (b) generating a methylation profile comprising the gene MGMT; (c) determining whether the subject has an MGMT promoter methylation; and (d) selecting subjects with an MGMT promoter methylation for treatment with about 2 mg/kg to about 10 mg/kg of 4-iodo-3-nitrobenzamide or a salt, metabolite or prodrug thereof; about 0 mg/m$^2$ to about 90 mg/m$^2$ of temozolomide; and radiation.

In some embodiments, disclosed herein is a method of treating a subject having glioblastoma characterized with an MGMT promoter methylation, comprising administering to the subject about 2 mg/kg to about 10 mg/kg of 4-iodo-3-nitrobenzamide or a salt, metabolite or prodrug thereof; about 0 mg/m$^2$ to about 90 mg/m$^2$ of temozolomide; and radiation, thereby treating the subject having glioblastoma characterized with an MGMT promoter methylation, wherein the subject is determined to have the MGMT promoter methylation by a) processing an extracted genomic DNA with a deaminating agent to generate a genomic DNA sample comprising deaminated nucleotides, wherein the extracted genomic DNA is obtained from a biological sample from the subject having glioblastoma or suspected of having glioblastoma; b) generating a methylation profile comprising the gene MGMT; and determining whether the subject has an MGMT promoter methylation.

In some embodiments, disclosed herein is a method of treating a subject with a treatment regimen comprising 4-iodo-3-nitrobenzamide or a salt, metabolite or prodrug thereof, wherein the subject is suffering from glioblastoma, the method comprising: determining whether the subject has an MGMT promoter methylation comprising: obtaining or having obtained a biological sample from the subject; and performing or having performed a methylation assay on the biological sample to determine if the subject has the MGMT promoter methylation; and if the subject has an MGMT promoter methylation, then administering the treatment regimen comprising 4-iodo-3-nitrobenzamide or a salt, metabolite or prodrug thereof to the subject, and if the subject does not have an MGMT promoter methylation, then administering a first-line treatment for glioblastoma to the subject, wherein a medium overall survival for the subject having an MGMT promoter methylation is extended following administration of the treatment regimen comprising 4-iodo-3-nitrobenzamide or a salt, metabolite or prodrug thereof than it would be if the first-line treatment were administered; wherein the treatment regimen comprising 4-iodo-3-nitrobenzamide or a salt, metabolite or prodrug thereof comprises: about 2 mg/kg to about 10 mg/kg of 4-iodo-3-nitrobenzamide or a salt, metabolite or prodrug thereof; about 0 mg/m$^2$ to about 90 mg/m$^2$ of temozolomide; and radiation.

$O^6$-alkylguanine-DNA alkyltransferase (also known as AGT, AGAT or MGMT) is a protein involved in repairing $O^6$-methylguanine to guanine and prevents mismatch and additional errors during DNA replication and transcription. The MGMT protein is encoded by the $O^6$-methylguanin-DNA-methyltransferase (MGMT) gene. In some instances, promoter methylation silences the MGMT gene. In such cases, the presence of methylation at the promoter region of the MGMT gene in a subject having glioblastoma is correlated with improved response outcome and longer overall survival relative to the response outcome of a subject having glioblastoma without the presence of methylation at the promoter region of the MGMT gene.

In some instances, the methylation profile further comprises the methylation status of TP53, PTEN, or a combination thereof. In some cases, the promoter region of TP53 and PTEN genes are methylated. In some cases, the methylation profile comprises the promoter methylation status of TP53, PTEN, or a combination thereof.

In some embodiments, the method further comprises determining the presence of a mutation in IDH1, IDH2, TP53, PTEN, or a combination thereof. In some instances, a mutation in the IDH1 gene correlates to a mutation at residue Arg-132 of the IDH1 protein (GenBank: CAG38738.1). In some cases, the mutation at position 132 is from Arg-132 to His, Ser, Cys, Gly, Val or Leu. In some instances, a mutation in the IDH2 gene correlates to a mutation at residue Arg-172 of the IDH2 protein (UniProtKB/Swiss-Prot: P48735.2). In some cases, the mutation at position 172 is from Arg-172 to Lys, Met or Gly. In some instances, one or more mutations are present in the TP53 gene. In some instances, one or more mutations are present in the PTEN gene. In some cases, the one or more mutations in the PTEN gene is located in exon 2, 3, 4, 5, 6, 7, or a combination thereof.

In some instances, the method comprises determining the presence of the promoter methylation of MGMT and the presence of a mutation in IDH1, IDH2, TP53, PTEN, or a combination thereof. In some cases, the method comprises determining the presence of the promoter methylation of MGMT and the presence of a mutation in TP53, PTEN, or a combination thereof. In other cases, the method comprises determining the presence of the promoter methylation of MGMT and the presence of a mutation in IDH1, IDH2, or a combination thereof.

In some embodiments, 4-iodo-3-nitrobenzamide or a salt, metabolite or prodrug thereof is administered from about 2 mg/kg to about 200 mg/kg. In some instances, 4-iodo-3-nitrobenzamide or a salt, metabolite or prodrug thereof is administered from about 2 mg/kg to about 150 mg/kg, from about 2 mg/kg to about 100 mg/kg, or from about 2 mg/kg to about 60 mg/kg. In some instances, 4-iodo-3-nitrobenzamide or a salt, metabolite or prodrug thereof is administered from about 5 mg/kg to about 150 mg/kg, from about 5 mg/kg to about 100 mg/kg, or from about 5 mg/kg to about 60 mg/kg. In some instances, 4-iodo-3-nitrobenzamide or a salt, metabolite or prodrug thereof is administered at a range of about 5 mg/kg to about 50 mg/kg, about 5 mg/kg to about 40 mg/kg, about 5 mg/kg to about 30 mg/kg, about 5 mg/kg to about 20 mg/kg, about 5 mg/kg to about 10 mg/kg, about 6 mg/kg to about 60 mg/kg, about 6 mg/kg to about 50 mg/kg, about 6 mg/kg to about 40 mg/kg, about 6 mg/kg to about 30 mg/kg, about 6 mg/kg to about 20 mg/kg, about 6 mg/kg to about 10 mg/kg, about 6 mg/kg to about 9 mg/kg, about 7 mg/kg to about 60 mg/kg, about 7 mg/kg to about 50 mg/kg, about 7 mg/kg to about 40 mg/kg, about 7 mg/kg to about 30 mg/kg, about 7 mg/kg to about 20 mg/kg, about 7 mg/kg to about 10 mg/kg, about 7 mg/kg to about 9 mg/kg, about 7 mg/kg to about 8 mg/kg, about 8 mg/kg to about 60 mg/kg, about 8 mg/kg to about 40 mg/kg, about 8 mg/kg to about 30 mg/kg, about 8 mg/kg to about 20 mg/kg, about 8 mg/kg to about 10 mg/kg, about 8 mg/kg to about 9 mg/kg, or about 8 mg/kg to about 8.6 mg/kg. In some embodiments, 4-iodo-3-nitrobenzamide or a salt, metabolite or prodrug thereof is administered at a range of about 6 mg/kg to about 40 mg/kg, about 6 mg/kg to about 30 mg/kg, about 6 mg/kg to about 20 mg/kg, about 6 mg/kg to about 10 mg/kg, about 6 mg/kg to about 9 mg/kg, about 7 mg/kg to about 30 mg/kg, about 7 mg/kg to about 20 mg/kg, about 7 mg/kg to about 9 mg/kg, about 7 mg/kg to about 8 mg/kg, about 8 mg/kg to about 20 mg/kg, about 8 mg/kg to about 9 mg/kg, or about 8 mg/kg to about 8.6 mg/kg. In some embodiments, 4-iodo-3-nitrobenzamide or a salt, metabolite or prodrug thereof is administered at a range of about 5 mg/kg to about 40 mg/kg. In some embodiments, 4-iodo-3-nitrobenzamide or a salt, metabolite or prodrug thereof is administered at a range of about 6 mg/kg to about 9 mg/kg. In some embodiments, 4-iodo-3-nitrobenzamide or a salt, metabolite or prodrug thereof is administered at a range of about 6 mg/kg to about 8.6 mg/kg. In some embodiments, 4-iodo-3-nitrobenzamide or a salt, metabolite or prodrug thereof is administered at a range of about 6 mg/kg to about 8 mg/kg. In some embodiments, 4-iodo-3-nitrobenzamide or a salt, metabolite or prodrug thereof is administered at a range of about 7 mg/kg to about 9 mg/kg. In some embodiments, 4-iodo-3-nitrobenzamide or a salt, metabolite or prodrug thereof is administered at a range of about 7 mg/kg to about 8.6 mg/kg. In some embodiments, 4-iodo-3-nitrobenzamide or a salt, metabolite or prodrug thereof is administered at a range of about 7 mg/kg to about 8 mg/kg. In some embodiments, 4-iodo-3-nitrobenzamide or a salt, metabolite or prodrug thereof is administered at a range of about 8 mg/kg to about 9 mg/kg. In some embodiments, 4-iodo-3-nitrobenzamide or a salt, metabolite or prodrug thereof is administered at a range of about 8 mg/kg to about 8.6 mg/kg.

In some embodiments, 4-iodo-3-nitrobenzamide or a salt, metabolite or prodrug thereof is administered at about 2 mg/kg, about 3 mg/kg, about 4 mg/kg, about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 2 mg/kg. In some embodiments, 4-iodo-3-nitrobenzamide or a salt, metabolite or prodrug thereof is administered at about 3 mg/kg. In some embodiments, 4-iodo-3-nitrobenzamide or a salt, metabolite or prodrug thereof is administered at about 4 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some embodiments, 4-iodo-3-nitrobenzamide or a salt, metabolite or prodrug thereof is administered at about 15 mg/kg. In some embodiments, 4-iodo-3-nitrobenzamide or a salt, metabolite or prodrug thereof is administered at about 20 mg/kg. In some embodiments, 4-iodo-3-nitrobenzamide or a salt, metabolite or prodrug thereof is administered at about 30 mg/kg. In some embodiments, 4-iodo-3-nitrobenzamide or a salt, metabolite or prodrug thereof is administered at about 40 mg/kg. In some embodiments, 4-iodo-3-nitrobenzamide or a salt, metabolite or prodrug thereof is administered at about 50 mg/kg. In some embodiments, 4-iodo-3-nitrobenzamide or a salt, metabolite or prodrug thereof is administered at about 60 mg/kg.

In some embodiments, 4-iodo-3-nitrobenzamide or a salt, metabolite or prodrug thereof is administered to a subject at one or more dosing schedules. In some embodiments, the dosing schedule comprises administering to the subject 4-iodo-3-nitrobenzamide or a salt, metabolite or prodrug thereof once per day, twice a week, three times a week, four times a week, five times a week, daily, every other day, once a month, twice a month, or every week. In some instances, the dosing schedule comprises administering to the subject 4-iodo-3-nitrobenzamide or a salt, metabolite or prodrug thereof once per day.

In some embodiments, the dosing schedule comprises administering to the subject 4-iodo-3-nitrobenzamide or a salt, metabolite or prodrug thereof continuously for about 1, 2, 3, 4, 5, 6, 7, 8, 9, 10, 11, 12 or more weeks. In some instances, the dosing schedule comprises administering to the subject 4-iodo-3-nitrobenzamide or a salt, metabolite or prodrug thereof continuously for about 1, 2, 3, 4, 5, 6, 7, 8, 9, 10 or more weeks. In some instances, the dosing schedule comprises administering to the subject 4-iodo-3-nitrobenzamide or a salt, metabolite or prodrug thereof continuously for about 1, 2, 3, 4, 5, 6 or more weeks. In some instances, the dosing schedule comprises administering to the subject 4-iodo-3-nitrobenzamide or a salt, metabolite or prodrug thereof continuously for about 5 weeks. In some instances, the dosing schedule comprises administering to the subject 4-iodo-3-nitrobenzamide or a salt, metabolite or prodrug thereof continuously for about 6 weeks. In some instances, the dosing schedule comprises administering to the subject 4-iodo-3-nitrobenzamide or a salt, metabolite or prodrug thereof continuously for about 7 weeks. In some instances, the dosing schedule comprises administering to the subject 4-iodo-3-nitrobenzamide or a salt, metabolite or prodrug thereof continuously for about 8 weeks. In some instances, the dosing schedule comprises administering to the subject 4-iodo-3-nitrobenzamide or a salt, metabolite or prodrug thereof continuously for about 9 weeks. In some instances, the dosing schedule comprises administering to the subject 4-iodo-3-nitrobenzamide or a salt, metabolite or prodrug thereof continuously for about 10 weeks. In some instances, a 5-week dosing schedule is considered as one cycle. In some instances, a 6-week dosing schedule is considered as one cycle. In some instances, a 7-week dosing schedule is considered as one cycle. In some instances, a 8-week dosing schedule is considered as one cycle. In some instances, a 9-week dosing schedule is considered as one cycle. In some instances, a 10-week dosing schedule is considered as one cycle. In some instances, a 11-week dosing schedule is considered as one cycle. In some instances, a 12-week dosing schedule is considered as one cycle.

In some embodiments, the dosing schedule comprises administering to the subject 4-iodo-3-nitrobenzamide or a salt, metabolite or prodrug thereof continuously for about 1, 2, 3, 4, 5, 6, 7, 8, 9, 10, 11, 12, 18, 24, 36, 48, or more months. In some instances, the dosing schedule comprises administering to the subject 4-iodo-3-nitrobenzamide or a salt, metabolite or prodrug thereof continuously for about 1, 2, 3, 4, 5, 6, 7, 8, 9, 10, 11, 12, or more months. In some instances, the dosing schedule comprises administering to the subject 4-iodo-3-nitrobenzamide or a salt, metabolite or prodrug thereof continuously for about 1, 2, 3, 4, 5, 6 or more months.

In some embodiments, the dosing schedule comprises administering to the subject 4-iodo-3-nitrobenzamide or a salt, metabolite or prodrug thereof continuously for about 1, 2, 3, 4, 5, 6, 7, 8, 9, 10 or more treatment cycles. In some instances, the dosing schedule comprises administering to the subject 4-iodo-3-nitrobenzamide or a salt, metabolite or prodrug thereof continuously for about 1, 2, 3, 4, 5, 6 or more treatment cycles. In some instances, the dosing schedule comprises administering to the subject 4-iodo-3-nitrobenzamide or a salt, metabolite or prodrug thereof continuously for about 1, 2, 3, 4 or more treatment cycles. In some instances, the dosing schedule comprises administering to the subject 4-iodo-3-nitrobenzamide or a salt, metabolite or prodrug thereof continuously for about 1 or more cycles. In some instances, the dosing schedule comprises administering to the subject 4-iodo-3-nitrobenzamide or a salt, metabolite or prodrug thereof continuously for about 2 or more cycles. In some instances, the dosing schedule comprises administering to the subject 4-iodo-3-nitrobenzamide or a salt, metabolite or prodrug thereof continuously for about 3 or more cycles. In some instances, the dosing schedule comprises administering to the subject 4-iodo-3-nitrobenzamide or a salt, metabolite or prodrug thereof continuously for about 4 or more cycles. In some instances, each treatment cycle is up to 28 days. In some cases, each treatment cycle is about 28 days. In other instances, each treatment cycle is up to 5 weeks. In other instances, each treatment cycle is about 5 weeks. In other instances, each treatment cycle is up to 6 weeks. In other instances, each treatment cycle is about 6 weeks. In other instances, each treatment cycle is up to 7 weeks. In other instances, each treatment cycle is about 7 weeks. In other instances, each treatment cycle is up to 8 weeks. In other instances, each treatment cycle is about 8 weeks. In other instances, each treatment cycle is up to 9 weeks. In other instances, each treatment cycle is about 9 weeks. In other instances, each treatment cycle is up to 10 weeks. In other instances, each treatment cycle is about 10 weeks. In some instances, a 11-week dosing schedule is considered as one cycle. In some instances, a 12-week dosing schedule is considered as one cycle.

In some embodiments, the dosing schedule comprises administering to the subject 4-iodo-3-nitrobenzamide or a salt, metabolite or prodrug thereof intermittently for about 1, 2, 3, 4, 5, 6, 7, 8, 9, 10, 11, 12 or more weeks. In some instances, the dosing schedule comprises administering to the subject 4-iodo-3-nitrobenzamide or a salt, metabolite or prodrug thereof intermittently for about 1, 2, 3, 4, 5, 6, 7, 8, 9, 10 or more weeks. In some instances, the dosing schedule comprises administering to the subject 4-iodo-3-nitrobenzamide or a salt, metabolite or prodrug thereof intermittently for about 1, 2, 3, 4, 5, 6 or more weeks. In some instances, the dosing schedule comprises administering to the subject 4-iodo-3-nitrobenzamide or a salt, metabolite or prodrug thereof intermittently for about 5 weeks. In some instances, the dosing schedule comprises administering to the subject 4-iodo-3-nitrobenzamide or a salt, metabolite or prodrug thereof intermittently for about 6 weeks. In some instances, the dosing schedule comprises administering to the subject 4-iodo-3-nitrobenzamide or a salt, metabolite or prodrug thereof intermittently for about 7 weeks. In some instances, the dosing schedule comprises administering to the subject 4-iodo-3-nitrobenzamide or a salt, metabolite or prodrug thereof intermittently for about 8 weeks. In some instances, the dosing schedule comprises administering to the subject 4-iodo-3-nitrobenzamide or a salt, metabolite or prodrug thereof intermittently for about 9 weeks. In some instances, the dosing schedule comprises administering to the subject 4-iodo-3-nitrobenzamide or a salt, metabolite or prodrug thereof intermittently for about 10 weeks. In some instances, a 5-week dosing schedule is considered as one cycle. In some instances, a 6-week dosing schedule is considered as one cycle. In some instances, a 7-week dosing schedule is considered as one cycle. In some instances, a 8-week dosing schedule is considered as one cycle. In some instances, a 9-week dosing schedule is considered as one cycle. In some instances, a 10-week dosing schedule is considered as one cycle.

In some embodiments, the dosing schedule comprises administering to the subject 4-iodo-3-nitrobenzamide or a salt, metabolite or prodrug thereof intermittently for about 1, 2, 3, 4, 5, 6, 7, 8, 9, 10, 11, 12, 18, 24, 36, 48, or more months. In some instances, the dosing schedule comprises administering to the subject 4-iodo-3-nitrobenzamide or a salt, metabolite or prodrug thereof intermittently for about 1, 2, 3, 4, 5, 6, 7, 8, 9, 10, 11, 12, or more months. In some instances, the dosing schedule comprises administering to the subject 4-iodo-3-nitrobenzamide or a salt, metabolite or prodrug thereof intermittently for about 1, 2, 3, 4, 5, 6 or more months.

In some embodiments, the dosing schedule comprises administering to the subject 4-iodo-3-nitrobenzamide or a salt, metabolite or prodrug thereof intermittently for about 1, 2, 3, 4, 5, 6, 7, 8, 9, 10 or more treatment cycles. In some instances, the dosing schedule comprises administering to the subject 4-iodo-3-nitrobenzamide or a salt, metabolite or prodrug thereof intermittently for about 1, 2, 3, 4, 5, 6 or more treatment cycles. In some instances, the dosing schedule comprises administering to the subject 4-iodo-3-nitrobenzamide or a salt, metabolite or prodrug thereof intermittently for about 1, 2, 3, 4 or more treatment cycles. In some instances, the dosing schedule comprises administering to the subject 4-iodo-3-nitrobenzamide or a salt, metabolite or prodrug thereof intermittently for about 1 or more cycles. In some instances, the dosing schedule comprises administering to the subject 4-iodo-3-nitrobenzamide or a salt, metabolite or prodrug thereof intermittently for about 2 or more cycles. In some instances, the dosing schedule comprises administering to the subject 4-iodo-3-nitrobenzamide or a salt, metabolite or prodrug thereof intermittently for about 3 or more cycles. In some instances, the dosing schedule comprises administering to the subject 4-iodo-3-nitrobenzamide or a salt, metabolite or prodrug thereof intermittently for about 4 or more cycles. In some instances, the dosing schedule comprises administering to the subject 4-iodo-3-nitrobenzamide or a salt, metabolite or prodrug thereof intermittently for about 5 or more cycles. In some instances, the dosing schedule comprises administering to the subject 4-iodo-3-nitrobenzamide or a salt, metabolite or prodrug thereof intermittently for about 6 or more cycles. In some instances, each treatment cycle is up to 28 days. In some cases, each treatment cycle is about 28 days. In other instances, each treatment cycle is up to 5 weeks. In other instances, each treatment cycle is about 5 weeks. In other instances, each treatment cycle is up to 6 weeks. In other instances, each treatment cycle is about 6 weeks. In other instances, each treatment cycle is up to 7 weeks. In other instances, each treatment cycle is about 7 weeks. In other instances, each treatment cycle is up to 8 weeks. In other instances, each treatment cycle is about 8 weeks. In other instances, each treatment cycle is up to 9 weeks. In other instances, each treatment cycle is about 9 weeks. In other instances, each treatment cycle is up to 10 weeks. In other instances, each treatment cycle is about 10 weeks.

In some cases, temozolomide is administered to a subject at a dosing range of 70 mg/m$^2$ to about 200 mg/m$^2$, about 70 mg/m$^2$ to about 80 mg/m$^2$, or about 150 mg/m$^2$ to about 200 mg/m$^2$. In some cases, temozolomide is administered to a subject at a dosing range of about 70 mg/m$^2$ to about 80 mg/m$^2$. In some cases, temozolomide is administered to a subject at a dosing range of about 150 mg/m$^2$ to about 200 mg/m$^2$. In some cases, the dosing range of about 150 mg/m$^2$ to about 200 mg/m$^2$ is administered to the subject as a maintenance regimen.

In some cases, temozolomide is administered to a subject at a dosing range of about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some cases, temozolomide is administered to a subject at a dose of about 60 mg/m$^2$. In some cases, temozolomide is administered to a subject at a dose of about 65 mg/m$^2$. In some cases, temozolomide is administered to a subject at a dose of about 70 mg/m$^2$. In some cases, temozolomide is administered to a subject at a dose of about 75 mg/m$^2$. In some cases, temozolomide is administered to a subject at a dose of about 80 mg/m$^2$. In some cases, temozolomide is administered to a subject at a dose of about 85 mg/m$^2$. In some cases, temozolomide is administered to a subject at a dose of about 90 mg/m$^2$. In some cases, temozolomide is administered to a subject at a dose of about 95 mg/m$^2$. In some cases, temozolomide is administered to a subject at a dose of about 100 mg/m$^2$.

In some cases, temozolomide is administered to a subject at a dosing range of 0 mg/m$^2$ to about 90 mg/m$^2$, about 0 mg/m$^2$ to about 80 mg/m$^2$, about 0 mg/m$^2$ to about 70 mg/m$^2$, about 10 mg/m$^2$ to about 80 mg/m$^2$, about 10 mg/m$^2$ to about 70 mg/m$^2$, about 10 mg/m$^2$ to about 60 mg/m$^2$, about 20 mg/m$^2$ to about 80 mg/m$^2$, about 20 mg/m$^2$ to about 70 mg/m$^2$, about 20 mg/m$^2$ to about 60 mg/m$^2$, about 30 mg/m$^2$ to about 80 mg/m$^2$, about 30 mg/m$^2$ to about 70 mg/m$^2$, or about 30 mg/m$^2$ to about 60 mg/m$^2$. In some cases, temozolomide is administered to a subject at a dosing range of 0 mg/m$^2$ to about 70 mg/m$^2$. In some cases, temozolomide is administered to a subject at a dosing range of 10 mg/m$^2$ to about 70 mg/m$^2$. In some cases, temozolomide is administered to a subject at a dosing range of 20 mg/m$^2$ to about 70 mg/m$^2$. In some cases, temozolomide is administered to a subject at a dosing range of 30 mg/m$^2$ to about 70 mg/m$^2$.

In some cases, temozolomide is administered to a subject at a dose of about 0 mg/m$^2$, 5 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 50 mg/m$^2$, 60 mg/m$^2$, 70 mg/m$^2$, 80 mg/m$^2$, or 90 mg/m$^2$. In some cases, temozolomide is administered to a subject at a dose of about 0 mg/m$^2$. In some cases, temozolomide is administered to a subject at a dose of about 5 mg/m$^2$. In some cases, temozolomide is administered to a subject at a dose of about 10 mg/m$^2$. In some cases, temozolomide is administered to a subject at a dose of about 15 mg/m$^2$. In some cases, temozolomide is administered to a subject at a dose of about 20 mg/m$^2$. In some cases, temozolomide is administered to a subject at a dose of about 25 mg/m$^2$. In some cases, temozolomide is administered to a subject at a dose of about 30 mg/m$^2$. In some cases, temozolomide is administered to a subject at a dose of about 35 mg/m$^2$. In some cases, temozolomide is administered to a subject at a dose of about 40 mg/m$^2$. In some cases, temozolomide is administered to a subject at a dose of about 50 mg/m$^2$. In some cases, temozolomide is administered to a subject at a dose of about 60 mg/m$^2$. In some cases, temozolomide is administered to a subject at a dose of about 70 mg/m$^2$. In some cases, temozolomide is administered to a subject at a dose of about 80 mg/m$^2$. In some cases, temozolomide is administered to a subject at a dose of about 90 mg/m$^2$.

In some instances, temozolomide is administered to the subject daily. In some cases, temozolomide is administered to the subject for about four, five, or about six weeks.

In some embodiments, temozolomide is not administered to the subject. In such cases, the method comprises, for example, selecting a subject having glioblastoma or suspected of having glioblastoma for treatment, which comprises processing an extracted genomic DNA with a deaminating agent to generate a genomic DNA sample comprising deaminated nucleotides, wherein the extracted genomic DNA is obtained from a biological sample from the subject having glioblastoma or suspected of having glioblastoma, generating a methylation profile comprising the gene MGMT, determining whether the subject has a MGMT promoter methylation, and administering to the subject about 2 mg/kg to about 10 mg/kg of 4-iodo-3-nitrobenzamide or a salt, metabolite or prodrug thereof and radiation.

In some cases, the total dose of radiation administered to a subject is up to 60 gray (Gy). In some cases, the total dose of radiation administered to a subject is up to 20 Gy, 30 Gy, 35 Gy, 40 Gy, 45 Gy, 50 Gy, 55 Gy, or 60 Gy. In some cases, the total dose of radiation administered to a subject is up to 20 Gy. In some cases, the total dose of radiation administered to a subject is up to 30 Gy. In some cases, the total dose of radiation administered to a subject is up to 35 Gy. In some cases, the total dose of radiation administered to a subject is up to 40 Gy. In some cases, the total dose of radiation administered to a subject is up to 45 Gy. In some cases, the total dose of radiation administered to a subject is up to 50 Gy. In some cases, the total dose of radiation administered to a subject is up to 55 Gy. In some cases, the total dose of radiation administered to a subject is up to 60 Gy. In some instances, the total radiation dose is the dose a subject receives over the course of a treatment cycle. In some instances, the treatment cycle is from 3 to 10 weeks. In some instances, the treatment cycle is from 4 to 10 weeks, from 5 to 10 weeks, from 6 to 10 weeks, from 7 to 10 weeks, from 4 to 9 weeks, from 5 to 9 weeks, from 6 to 9 weeks, from 5 to 8 weeks, or from 6 to 8 weeks. In some instances, the treatment cycle is about 3 weeks. In some instances, the treatment cycle is about 4 weeks. In some instances, the treatment cycle is about 5 weeks. In some instances, the treatment cycle is about 6 weeks. In some instances, the treatment cycle is about 7 weeks. In some instances, the treatment cycle is about 8 weeks. In some instances, the treatment cycle is about 9 weeks. In some instances, the treatment cycle is about 10 weeks.

In some embodiments, a combination of 4-iodo-3-nitrobenzamide or a salt, metabolite or prodrug thereof; temozolomide; and radiation is administered to a subject. In some embodiments, the combination is administered during a treatment phase (also referred to as initiation phase or initiation cycle). In some instances, the treatment phase comprises an administration phase and a rest phase. In some cases, the administration phase comprises about two, three, four, five, six, seven, eight, nine, ten, or more weeks in which the combination of 4-iodo-3-nitrobenzamide or a salt, metabolite or prodrug thereof; temozolomide; and radiation is administered to the subject. In some instances, the rest phase comprises about three, four, five, six or more weeks in which no treatment is administered to the subject. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some instances, 4-iodo-3-nitrobenzamide or a salt, metabolite or prodrug thereof is administered about once per day. In some cases, 4-iodo-3-nitrobenzamide or a salt, metabolite or prodrug thereof is administered about twice a week. In additional cases, 4-iodo-3-nitrobenzamide or a salt, metabolite or prodrug thereof is administered about once per day and twice a week. In some cases, temozolomide is administered to a subject at a dose of about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some cases, temozolomide is administered to a subject at a dose of about 60 mg/m$^2$. In some cases, temozolomide is administered to a subject at a dose of about 65 mg/m$^2$. In some cases, temozolomide is administered to a subject at a dose of about 70 mg/m$^2$. In some cases, temozolomide is administered to a subject at a dose of about 75 mg/m$^2$. In some cases, temozolomide is administered to a subject at a dose of about 80 mg/m$^2$. In some cases, temozolomide is administered to a subject at a dose of about 85 mg/m$^2$. In some cases, temozolomide is administered to a subject at a dose of about 90 mg/m$^2$. In some cases, temozolomide is administered to a subject at a dose of about 95 mg/m$^2$. In some cases, temozolomide is administered to a subject at a dose of about 100 mg/m$^2$. In some embodiments, temozolomide is administered daily. In some cases, the total dose of radiation administered to a subject is up to 60 gray (Gy). In some cases, the total dose of radiation administered to a subject is up to 20 Gy, 30 Gy, 35 Gy, 40 Gy, 45 Gy, 50 Gy, 55 Gy, or 60 Gy. In some cases, the total dose of radiation administered to a subject is up to 20 Gy. In some cases, the total dose of radiation administered to a subject is up to 30 Gy. In some cases, the total dose of radiation administered to a subject is up to 35 Gy. In some cases, the total dose of radiation administered to a subject is up to 40 Gy. In some cases, the total dose of radiation administered to a subject is up to 45 Gy. In some cases, the total dose of radiation administered to a subject is up to 50 Gy. In some cases, the total dose of radiation administered to a subject is up to 55 Gy. In some cases, the total dose of radiation administered to a subject is up to 60 Gy.

In some embodiments, a combination of 4-iodo-3-nitrobenzamide or a salt, metabolite or prodrug thereof; temozolomide; and radiation is administered to a subject during the treatment phase for about six weeks followed by about four weeks of rest phase (or no treatment). In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some instances, 4-iodo-3-nitrobenzamide or a salt, metabolite or prodrug thereof is administered about once per day. In some cases, 4-iodo-3-nitrobenzamide or a salt, metabolite or prodrug thereof is administered about twice a week. In additional cases, 4-iodo-3-nitrobenzamide or a salt, metabolite or prodrug thereof is administered about once per day and twice a week. In some cases, temozolomide is administered to a subject at a dose of about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some cases, temozolomide is administered to a subject at a dose of about 60 mg/m$^2$. In some cases, temozolomide is administered to a subject at a dose of about 65 mg/m$^2$. In some cases, temozolomide is administered to a subject at a dose of about 70 mg/m$^2$. In some cases, temozolomide is administered to a subject at a dose of about 75 mg/m$^2$. In some cases, temozolomide is administered to a subject at a dose of about 80 mg/m$^2$. In some cases, temozolomide is administered to a subject at a dose of about 85 mg/m$^2$. In some cases, temozolomide is administered to a subject at a dose of about 90 mg/m$^2$. In some cases, temozolomide is administered to a subject at a dose of about 95 mg/m$^2$. In some cases, temozolomide is administered to a subject at a dose of about 100 mg/m$^2$. In some embodiments, temozolomide is administered daily. In some cases, the total dose of radiation administered to a subject is up to 60 gray (Gy). In some cases, the total dose of radiation administered to a subject is up to 20 Gy, 30 Gy, 35 Gy, 40 Gy, 45 Gy, 50 Gy, 55 Gy, or 60 Gy. In some cases, the total dose of radiation administered to a subject is up to 20 Gy. In some cases, the total dose of radiation administered to a subject is up to 30 Gy. In some cases, the total dose of radiation administered to a subject is up to 35 Gy. In some cases, the total dose of radiation administered to a subject is up to 40 Gy. In some cases, the total dose of radiation administered to a subject is up to 45 Gy. In some cases, the total dose of radiation administered to a subject is up to 50 Gy. In some cases, the total dose of radiation administered to a subject is up to 55 Gy. In some cases, the total dose of radiation administered to a subject is up to 60 Gy.

In some embodiments, a combination of 4-iodo-3-nitrobenzamide or a salt, metabolite or prodrug thereof; temozolomide; and radiation is administered to a subject during the treatment phase for about six weeks followed by about four weeks of rest phase (or no treatment). In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some cases, 4-iodo-3-nitrobenzamide or a salt, metabolite or prodrug thereof is administered about once per day and twice a week. In some cases, temozolomide is administered to a subject at a dose of about 60 mg/m$^2$, about 65 mg/m$^2$, about 70 mg/m$^2$, about 75 mg/m$^2$, about 80 mg/m$^2$, about 85 mg/m$^2$, about 90 mg/m$^2$, about 95 mg/m$^2$, or about 100 mg/m$^2$. In some cases, temozolomide is administered to a subject at a dose of about 60 mg/m$^2$. In some cases, temozolomide is administered to a subject at a dose of about 65 mg/m$^2$. In some cases, temozolomide is administered to a subject at a dose of about 70 mg/m$^2$. In some cases, temozolomide is administered to a subject at a dose of about 75 mg/m$^2$. In some cases, temozolomide is administered to a subject at a dose of about 80 mg/m$^2$. In some cases, temozolomide is administered to a subject at a dose of about 85 mg/m$^2$. In some cases, temozolomide is administered to a subject at a dose of about 90 mg/m$^2$. In some cases, temozolomide is administered to a subject at a dose of about 95 mg/m$^2$. In some cases, temozolomide is administered to a subject at a dose of about 100 mg/m$^2$. In some embodiments, temozolomide is administered daily. In some cases, the total dose of radiation administered to a subject is up to 60 gray (Gy). In some cases, the total dose of radiation administered to a subject is up to 20 Gy, 30 Gy, 35 Gy, 40 Gy, 45 Gy, 50 Gy, 55 Gy, or 60 Gy. In some cases, the total dose of radiation administered to a subject is up to 20 Gy. In some cases, the total dose of radiation administered to a subject is up to 30 Gy. In some cases, the total dose of radiation administered to a subject is up to 35 Gy. In some cases, the total dose of radiation administered to a subject is up to 40 Gy. In some cases, the total dose of radiation administered to a subject is up to 45 Gy. In some cases, the total dose of radiation administered to a subject is up to 50 Gy. In some cases, the total dose of radiation administered to a subject is up to 55 Gy. In some cases, the total dose of radiation administered to a subject is up to 60 Gy.

In some embodiments, a combination of 4-iodo-3-nitrobenzamide or a salt, metabolite or prodrug thereof; and radiation is administered to a subject during the treatment phase for about six weeks followed by about four weeks of rest phase (or no treatment). In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some instances, 4-iodo-3-nitrobenzamide or a salt, metabolite or prodrug thereof is administered about once per day. In some cases, 4-iodo-3-nitrobenzamide or a salt, metabolite or prodrug thereof is administered about twice a week. In additional cases, 4-iodo-3-nitrobenzamide or a salt, metabolite or prodrug thereof is administered about once per day and twice a week. In some cases, the total dose of radiation administered to a subject is up to 60 gray (Gy). In some cases, the total dose of radiation administered to a subject is up to 20 Gy, 30 Gy, 35 Gy, 40 Gy, 45 Gy, 50 Gy, 55 Gy, or 60 Gy. In some cases, the total dose of radiation administered to a subject is up to 20 Gy. In some cases, the total dose of radiation administered to a subject is up to 30 Gy. In some cases, the total dose of radiation administered to a subject is up to 35 Gy. In some cases, the total dose of radiation administered to a subject is up to 40 Gy. In some cases, the total dose of radiation administered to a subject is up to 45 Gy. In some cases, the total dose of radiation administered to a subject is up to 50 Gy. In some cases, the total dose of radiation administered to a subject is up to 55 Gy. In some cases, the total dose of radiation administered to a subject is up to 60 Gy.

In some embodiments, a combination of 4-iodo-3-nitrobenzamide or a salt, metabolite or prodrug thereof; radiation, and an additional chemotherapeutic agent is administered to a subject during the treatment phase for about six weeks followed by about four weeks of rest phase (or no treatment). In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some instances, 4-iodo-3-nitrobenzamide or a salt, metabolite or prodrug thereof is administered about once per day. In some cases, 4-iodo-3-nitrobenzamide or a salt, metabolite or prodrug thereof is administered about twice a week. In additional cases, 4-iodo-3-nitrobenzamide or a salt, metabolite or prodrug thereof is administered about once per day and twice a week. In some cases, the total dose of radiation administered to a subject is up to 60 gray (Gy). In some cases, the total dose of radiation administered to a subject is up to 20 Gy, 30 Gy, 35 Gy, 40 Gy, 45 Gy, 50 Gy, 55 Gy, or 60 Gy. In some cases, the total dose of radiation administered to a subject is up to 20 Gy. In some cases, the total dose of radiation administered to a subject is up to 30 Gy. In some cases, the total dose of radiation administered to a subject is up to 35 Gy. In some cases, the total dose of radiation administered to a subject is up to 40 Gy. In some cases, the total dose of radiation administered to a subject is up to 45 Gy. In some cases, the total dose of radiation administered to a subject is up to 50 Gy. In some cases, the total dose of radiation administered to a subject is up to 55 Gy. In some cases, the total dose of radiation administered to a subject is up to 60 Gy. In some instances, the additional chemotherapeutic agent comprises procarbazine, carmustine (BCNU), iomustine (CCNU), or vincristine. In some instances, the additional chemotherapeutic agent does not include temozolomide.

In some embodiments, upon completion of a treatment phase or initiation cycle, a maintenance cycle is then initiated. In some instances, the maintenance cycle comprises about 1-10, 1-8, or 1-6 cycles. In some cases, a cycle is about 28 days. In some cases, a cycle is about 4 weeks. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some instances, 4-iodo-3-nitrobenzamide or a salt, metabolite or prodrug thereof is administered about once per day. In some cases, 4-iodo-3-nitrobenzamide or a salt, metabolite or prodrug thereof is administered about twice a week. In additional cases, 4-iodo-3-nitrobenzamide or a salt, metabolite or prodrug thereof is administered about once per day and twice a week. In some cases, temozolomide is administered to a subject at a dosing range of 70 mg/m$^2$ to about 200 mg/m$^2$, about 70 mg/m$^2$ to about 80 mg/m$^2$, or about 150 mg/m$^2$ to about 200 mg/m$^2$. In some cases, temozolomide is administered to a subject at a dosing range of about 150 mg/m$^2$ to about 200 mg/m$^2$. In some cases, temozolomide is administered on Days 1-5 of each cycle. In some cases, the administration of temozolomide is repeated every 28 days.

In some instances, the maintenance cycle comprises about 1-6 cycles. In some cases, a cycle is about 28 days. In some cases, a cycle is about 4 weeks. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 100 mg/kg, about 150 mg/kg, or about 200 mg/kg. In some embodiments, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, or about 40 mg/kg. In some embodiments, 4-iodo-3-nitrobenzamide or a salt, metabolite or prodrug thereof is administered at about 5 mg/kg. In some embodiments, 4-iodo-3-nitrobenzamide or a salt, metabolite or prodrug thereof is administered at about 6 mg/kg. In some embodiments, 4-iodo-3-nitrobenzamide or a salt, metabolite or prodrug thereof is administered at about 7 mg/kg. In some embodiments, 4-iodo-3-nitrobenzamide or a salt, metabolite or prodrug thereof is administered at about 8 mg/kg. In some embodiments, 4-iodo-3-nitrobenzamide or a salt, metabolite or prodrug thereof is administered at about 8.5 mg/kg. In some embodiments, 4-iodo-3-nitrobenzamide or a salt, metabolite or prodrug thereof is administered at about 8.6 mg/kg. In some embodiments, 4-iodo-3-nitrobenzamide or a salt, metabolite or prodrug thereof is administered at about 9 mg/kg. In some embodiments, 4-iodo-3-nitrobenzamide or a salt, metabolite or prodrug thereof is administered at about 10 mg/kg. In some instances, 4-iodo-3-nitrobenzamide or a salt, metabolite or prodrug thereof is administered about once per day. In some cases, 4-iodo-3-nitrobenzamide or a salt, metabolite or prodrug thereof is administered about twice a week. In additional cases, 4-iodo-3-nitrobenzamide or a salt, metabolite or prodrug thereof is administered about once per day and twice a week. In some cases, temozolomide is administered to a subject at a dosing range of 70 mg/m$^2$ to about 200 mg/m$^2$, about 70 mg/m$^2$ to about 80 mg/m$^2$, or about 150 mg/m$^2$ to about 200 mg/m$^2$. In some cases, temozolomide is administered to a subject at a dosing range of about 150 mg/m$^2$ to about 200 mg/m$^2$. In some cases, temozolomide is administered on Days 1-5 of each cycle. In some cases, the administration of temozolomide is repeated every 28 days.

In some embodiments, the method further comprises determining the expression level of at least one gene selected from thioredoxin reductase 2 (TXNRD2), thioredoxin 2 (TXN2), methionine sulfoxide reductase B3 (MSRB3), methionine sulfoxide reductase A (MSRA), and glutathione transferase zeta 1 (GSTZ1) by i) contacting at least one gene selected from TXNRD2, TXN2, MSRB3, MSRA, and GSTZ1 with a set of primers to produce amplified nucleic acids, wherein the at least one gene is isolated from a tumor sample obtained from the subject; and ii) determining the level of the amplified nucleic acids in the tumor sample relative to a control; wherein an elevated expression of the genes indicate that the subject is responsive to the treatment.

In some embodiments, the level of at least one gene selected from TXNRD2, TXN2, MSRB3 and MSRA is determined. In some cases, the level of two or more genes selected from TXNRD2, TXN2, MSRB3 and MSRA are determined. In some cases, the level of TXNRD2 is determined. In some cases, the level of TXN2 is determined. In some cases, the level of MSRB3 is determined. In some cases, the level of MSRA is determined. In some cases, the level of TXNRD2, TXN2, MSRB3 and MSRA are determined.

In some embodiments, the level of the amplified nucleic acids from at least one gene selected from TXNRD2, TXN2, MSRB3, MSRA and GSTZ1 correlates to a decreased risk of disease progression.

In some embodiments, the method further comprises determining the level of amplified nucleic acids from at least one gene selected from NAD(P)H dehydrogenase quinone 2 (NQO2), glutathione S-transferase theta 2 (GSTT2), glutathione S-transferase M3 (GSTM3), glutaredoxin (GLRX), selenoprotein O (SELO), paraoxonase 1 (PON1), glutathione S-transferase omega 1 (GSTO1), glutaredoxin 3 (GLRX3), selenoprotein X 1 (SEPX1), and thioredoxin reductase 1 (TXNRD1) and comparing the level with a control.

In some embodiments, the level of at least one gene selected from NQO2, GSTT2, GSTM3, GLRX, GSTO1, GLRX3 and TXNRD1 is determined. In some instances, the level of at least one gene selected from NQO2, GSTT2, GSTM3, GLRX, GSTO1 and GLRX3 is determined. In some instances, the level of at least one gene selected from GSTT2, GSTM3, GLRX, GSTO1 and GLRX3 is determined. In some instances, the level of at least one gene selected from GSTT2, GSTM3, and GSTO1 is determined. In some instances, the level of at least one gene selected from NQO2, SELO, PON1, SEPX1 and TXNRD1 is determined. In some instances, the level of at least one gene selected from SELO, PON1, SEPX1 and TXNRD1 is determined. In some instances, the level of at least one gene selected from SELO, PON1 and SEPX1 is determined. In some instances, the level of NQO2 is determined. In some instances, the level of GSTT2 is determined. In some instances, the level of GSTM3 is determined. In some instances, the level of GLRX is determined. In some instances, the level of GSTO1 is determined. In some instances, the level of GLRX3 is determined. In some instances, the level of TXNRD1 is determined.

In some cases, the treatment with 4-iodo-3-nitrobenzamide or a salt, metabolite or prodrug thereof is discontinued if the level of amplified nucleic acids is greater than the level in the control.

In some cases, the level of amplified nucleic acids greater than the level in the control correlates to an increased risk of disease progression.

In some embodiments, a subject is diagnosed with a primary glioblastoma. In other embodiments, a subject is diagnosed with a secondary tumor. In some cases, a subject is diagnosed with a grade I or grade II glioblastoma. In other cases, a subject is diagnosed with a grade III or a grade IV glioblastoma. In some cases, the glioblastoma is a metastasized glioblastoma.

In some embodiments, the combination of 4-iodo-3-nitrobenzamide or a metabolite thereof, temozolomide and radiation extends the median overall survival. In some cases, the median overall survival is extended to about 16 to about 24 months. In some cases, the median overall survival is extended to about 21 months.

In some embodiments, the combination of 4-iodo-3-nitrobenzamide or a metabolite thereof, and radiation extends the median overall survival.

In some embodiments, the hazard rate of death is reduced from about 0.6 to about 0.42, with a combination of 4-iodo-3-nitrobenzamide or a metabolite thereof, temozolomide and radiation.

In some embodiments, the hazard rate of death is reduced with a combination of 4-iodo-3-nitrobenzamide or a metabolite thereof, and radiation.

In some embodiments, the combination of 4-iodo-3-nitrobenzamide or a metabolite thereof, radiation, and optionally temozolomide increases the complete response or partial response of a subject administered with the combination, relative to a second subject who is not administered with the combination.

In some embodiments, the combination of 4-iodo-3-nitrobenzamide or a metabolite thereof, radiation, and optionally temozolomide extends the progression-free survival (PFS) of a subject administered with the combination, relative to a second subject who is not administered with the combination.

Samples and Detection Methods
Samples

In some embodiments, a sample described herein is obtained from a mammalian source. In some instances, the mammalian source comprises human and non-human primates. In other cases, the mammalian source comprises a rodent (e.g., mouse, rat), cat, rabbit, dog, and the like.

In some cases, a sample described herein is a tissue sample. In some cases, the sample is a biopsy sample. In some cases, the sample is a tumor sample, e.g., a tumor sample obtained from brain cancer, bladder cancer, breast cancer, colorectal cancer, lung cancer, or prostate cancer.

In some cases, a sample described herein is a liquid sample. In some cases, the liquid sample comprises blood and other liquid samples of biological origin (including, but not limited to, peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood). In some embodiments, the sample is blood, a blood derivative or a blood fraction, e.g., serum or plasma. In some embodiments, the liquid sample also encompasses a sample that has been manipulated in any way after their procurement, such as by centrifugation, filtration, precipitation, dialysis, chromatography, treatment with reagents, washed, or enriched for certain cell populations.

In some embodiments, a sample described herein is a cell sample, e.g., obtained from a tumor or a cancer cell line. In some instances, the cell sample is obtained from cells of brain cancer, bladder cancer, breast cancer, colorectal cancer, lung cancer, prostate cancer, large granular lymphocytic leukemia, T-cell acute lymphoblastic leukemia (T-ALL), T-cell prolymphocytic leukemia (T-PLL) or a melanoma.

In some instances, a sample described herein is a cell-free sample.

In some embodiments, the samples are obtained from the individual by any suitable means of obtaining the sample using well-known and routine clinical methods. Procedures for obtaining fluid samples from an individual are well known. For example, procedures for drawing and processing whole blood and lymph are well-known and can be employed to obtain a sample for use in the methods provided. Typically, for collection of a blood sample, an anticoagulation agent (e.g., EDTA, or citrate and heparin or CPD (citrate, phosphate, dextrose) or comparable substances) is added to the sample to prevent coagulation of the blood. In some examples, the blood sample is collected in a collection tube that contains an amount of EDTA to prevent coagulation of the blood sample.

In some embodiments, the collection of a sample from the subject is performed at regular intervals, such as, for example, one day, two days, three days, four days, five days, six days, one week, two weeks, weeks, four weeks, one month, two months, three months, four months, five months, six months, one year, daily, weekly, bimonthly, quarterly, biyearly or yearly.

In some embodiments, the collection of a sample is performed at a predetermined time or at regular intervals relative to treatment with 4-iodo-3-nitrobenzamide or a salt, metabolite or prodrug thereof. In some cases, the collection of a sample is performed at a predetermined time or at regular intervals relative to treatment with 4-iodo-3-nitrobenzamide or a salt, metabolite or prodrug thereof and an additional therapeutic agent described herein.

Detection Methods

In some embodiments, methods of detecting the expression level of one or more biomarkers described herein include, but are not limited to, Western blots, Northern blots, Southern blots, enzyme-linked immunosorbent assay (ELISA), immunoprecipitation, immunofluorescence, radio-immunoassay, immunocytochemistry, nucleic acid hybridization techniques, nucleic acid reverse transcription methods, nucleic acid amplification methods, or a combination thereof. In some cases, the biomarkers described herein comprise genes: TXNRD2, TXN2, MSRB3, MSRA, GSTZ1, NQO2, GSTT2, GSTM3, GLRX, GSTO1, GLRX3, TXNRD1, SELO, PON1, and SEPX1 and the proteins encoded by the respective genes.

In some embodiments, the expression level of one or more biomarkers described herein is determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA is utilized for the purification of RNA (see, e.g., Ausubel et al., ed. (1987-1999) Current Protocols in Molecular Biology (John Wiley & Sons, New York). Additionally, large numbers of tissue samples are readily processed using techniques well known to those of skill in the art, such as, for example, the single-step RNA isolation process disclosed in U.S. Pat. No. 4,843,155.

As used herein, the term "nucleic acid probe" refers to any molecule that is capable of selectively binding to a specifically intended target nucleic acid molecule, for example, a nucleotide transcript. Suitable methods for synthesizing nucleic acid probes are also described in Caruthers, Science, 230:281-285, (1985). In some instances, probes suitable for use herein include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. In some cases, probes are single stranded. In other cases, probes are double stranded. Exemplary nucleotide analogs include phosphate esters of deoxyadenosine, deoxycytidine, deoxyguanosine, deoxythymidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RN A.

In some cases, a probe used for detection optionally includes a detectable label, such as a radiolabel, fluorescent label, or enzymatic label. See for example Lancaster et al., U.S. Pat. No. 5,869,717. In some embodiments, the probe is fluorescently labeled. Fluorescently labeled nucleotides may be produced by various techniques, such as those described in Kambara et al., Bio/Technol., 6:816-21, (1988); Smith et al., Nucl. Acid Res., 13:2399-2412, (1985); and Smith et al., Nature, 321: 674-679. (1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach, IRL Press, Oxford, (1991); Zuckerman et al., Polynucleotides Res., 15: 5305-5321, (1987); Sharma et al., Polynucleotides Res., 19:3019, (1991); Giusti et al., PCR Methods and Applications, 2:223-227, (1993); Fung et al. (U.S. Pat. No. 4,757,141); Stabinsky (U.S. Pat. No. 4,739,044); Agrawal et al., Tetrahedron Letters, 31: 1543-1546, (1990); Sproat et al., Polynucleotides Res., 15:4837, (1987); and Nelson et al., Polynucleotides Res., 17:7187-7194, (1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

In some cases, the detectable label attached to the probe is either directly or indirectly detectable. In some embodiments, the exact label may be selected based, at least in part, on the particular type of detection method used. Exemplary detection methods include radioactive detection, optical absorbance detection, e.g., UV-visible absorbance detection, optical emission detection, e.g., fluorescence; phosphorescence or chemiluminescence; Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; alexa; fluorescien; conjugated multi-dyes; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumrarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives: erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehydyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolta Blue; phthalo cyanine; and naphthalo cyanine. Labels other than fluorescent labels are contemplated by the invention, including other optically-detectable labels.

Detection of a bound probe may be measured using any of a variety of techniques dependent upon the label used, such as those known to one of skill in the art. Exemplary detection methods include radioactive detection, optical absorbance detection, e.g., UV-visible absorbance detection, optical emission detection, e.g., fluorescence or chemiluminescence. Devices capable of sensing fluorescence from a single molecule include scanning tunneling microscope (siM) and the atomic force microscope (AFM). Hybridization patterns may also be scanned using a CCI) camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993)), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc. (Watertown, Mass. on the World Wide Web at genscan.com), Genix Technologies (Waterloo, Ontario, Canada; on the World Wide Web at confocal.com), and Applied Precision Inc.

In certain embodiments, the target nucleic acid or nucleic acid ligand or both are quantified using methods known in the art. For example, isolated mRNA are used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, biomarker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan System).

Modifications or expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression also comprises using nucleic acid probes in solution.

In some embodiments, microarrays are used to determine expression or presence of one or more biomarkers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992, 6,020,135, 6,033,860, 6,344,316, and U.S. Pat. Application 20120208706. High-density oligonucleotide arrays are particularly useful for determining the gene expression profile for a large number of RNA's in a sample. Exemplary microarray chips include FoundationOne and FoundationOne Heme from Foundation Medicine, Inc; GeneChip® Human Genome U133 Plus 2.0 array from Affymetrix; and Human DiscoveryMAP® 250+ v. 2.0 from Myraid RBM.

Techniques for the synthesis of these arrays using mechanical synthesis methods are described in, e.g., U.S. Pat. No. 5,384,261. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. In some embodiments, arrays are packaged in such a manner as to allow for diagnostics or other manipulation of an all-inclusive device.

In some instances, a method for quantitation is quantitative polymerase chain reaction (QPCR). As used herein, "QPCR" refers to a PCR reaction performed in such a way and under such controlled conditions that the results of the assay are quantitative, that is, the assay is capable of quantifying the amount or concentration of a nucleic acid ligand present in the test sample. QPCR is a technique based on the polymerase chain reaction, and is used to amplify and simultaneously quantify a targeted nucleic acid molecule. QPCR allows for both detection and quantification (as absolute number of copies or relative amount when normalized to DNA input or additional normalizing genes) of a specific sequence in a DNA sample. The procedure follows the general principle of PCR, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), (2006)), Heid et al. (Genome Research 986-994, (1996)), Sambrook and Russell (Quantitative PCR, Cold Spring Harbor Protocols, (2006)), and Higuchi (U.S. Pat. Nos. 6,171,785 and 5,994,056).

In some embodiments, the expression level is a protein expression and the level of the protein expression of a gene described herein is detected. In some cases, the detection method comprises contacting a biological sample with an antibody that specifically recognizes or specifically binds to a protein (e.g., a protein encoded by TXNRD2, TXN2, MSRB3, MSRA, GSTZ1, NQO2, GSTT2, GSTM3, GLRX, GSTO1, GLRX3, TXNRD1, SELO, PON1, or SEPX1) and detecting the complex between the antibody and the protein. In some cases, the antibody is an anti-TXNRD2 antibody. In some cases, the antibody is an anti-TXN2 antibody. In some instances, the antibody is an anti-MSRB3 antibody. In some cases, the antibody is an anti-MSRA antibody. In some cases, the antibody is an anti-GSTZ1 antibody. In some cases, the antibody is an anti-NQO2 antibody. In some cases, the antibody is an anti-GSTT2 antibody. In some cases, the antibody is an anti-GSTM3 antibody. In some cases, the antibody is an anti-GLRX antibody. In some cases, the antibody is an anti-GSTO1 antibody. In some cases, the antibody is an anti-GLRX3 antibody. In some cases, the antibody is an anti-TXNRD1 antibody. In some cases, the antibody is an anti-SELO antibody. In some cases, the antibody is an anti-PON1 antibody. In some cases, the antibody is an anti-SEPX1 antibody. In some cases, the level of the protein expression is determined by immunoassays including, but not limited to, radioimmunoassay, Western blot assay, ELISA, immunofluorescent assay, enzyme immunoassay, immunoprecipitation, chemiluminescent assay, immunohistochemical assay, dot blot assay, and slot blot assay.

In some instances, methylation analysis is carried out by any means known in the art. A variety of methylation analysis procedures are known in the art and may be used to practice the methods disclosed herein. These assays allow for determination of the methylation state of one or a plurality of CpG sites within a tissue sample. In addition, these methods may be used for absolute or relative quantification of methylated nucleic acids. Such methylation assays involve, among other techniques, two major steps. The first step is a methylation specific reaction or separation, such as (i) bisulfite treatment, (ii) methylation specific binding, or (iii) methylation specific restriction enzymes.

The second major step involves (i) amplification and detection, or (ii) direct detection, by a variety of methods such as (a) PCR (sequence-specific amplification) such as Taqman®, (b) DNA sequencing of untreated and bisulfite-treated DNA, (c) sequencing by ligation of dye-modified probes (including cyclic ligation and cleavage), (d) pyrosequencing, (e) single-molecule sequencing, (f) mass spectroscopy, or (g) Southern blot analysis.

Additionally, restriction enzyme digestion of PCR products amplified from bisulfite-converted DNA may be used, e.g., the method described by Sadri and Hornsby (1996, Nucl. Acids Res. 24:5058-5059), or COBRA (Combined Bisulfite Restriction Analysis) (Xiong and Laird, 1997, Nucleic Acids Res. 25:2532-2534). COBRA analysis is a quantitative methylation assay useful for determining DNA methylation levels at specific gene loci in small amounts of genomic DNA. Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Frommer et al, 1992, Proc. Nat. Acad. Sci. USA, 89, 1827-1831). PCR amplification of the bisulfite converted DNA is then performed using primers specific for the CpG sites of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples. Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfo nation buffer; DNA recovery reagents or kits (e.g., precipitation, ultrafiltration, affinity column); desulfonation buffer; and DNA recovery components.

In an embodiment, the methylation profile of selected CpG sites is determined using methylation-Specific PCR (MSP). MSP allows for assessing the methylation status of virtually any group of CpG sites within a CpG island, independent of the use of methylation-sensitive restriction enzymes (Herman et al, 1996, Proc. Nat. Acad. Sci. USA, 93, 9821-9826; U.S. Pat. Nos. 5,786,146, 6,017,704, 6,200, 756, 6,265,171 (Herman and Baylin); U.S. Pat. Pub. No. 2010/0144836 (Van Engeland et al); which are hereby incorporated by reference in their entirety). Briefly, DNA is modified by a deaminating agent such as sodium bisulfite to convert unmethylated, but not methylated cytosines to uracil, and subsequently amplified with primers specific for methylated versus unmethylated DNA. In some instances, typical reagents (e.g., as might be found in a typical MSP-based kit) for MSP analysis include, but are not limited to: methylated and unmethylated PCR primers for specific gene (or methylation-altered DNA sequence or CpG island), optimized PCR buffers and deoxynucleotides, and specific probes. One may use quantitative multiplexed methylation specific PCR (QM-PCR), as described by Fackler et al. Fackler et al, 2004, Cancer Res. 64(13) 4442-4452; or Fackler et al, 2006, Clin. Cancer Res. 12(11 Pt 1) 3306-3310.

In an embodiment, the methylation profile of selected CpG sites is determined using MethyLight and/or Heavy Methyl Methods. The MethyLight and Heavy Methyl assays are a high-throughput quantitative methylation assay that utilizes fluorescence-based real-time PCR (Taq Man®) technology that requires no further manipulations after the PCR step (Eads, C. A. et al, 2000, Nucleic Acid Res. 28, e 32; Cottrell et al, 2007, J. Urology 177, 1753, U.S. Pat. No. 6,331,393 (Laird et al), the contents of which are hereby incorporated by reference in their entirety). Briefly, the MethyLight process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. In some cases, sequence discrimination occurs either at the level of the amplification process or at the level of the fluorescence detection process, or both. In some cases, the MethyLight assay is used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites. Typical reagents (e.g., as might be found in a typical MethyLight-based kit) for MethyLight analysis may include, but are not limited to: PCR primers for specific gene (or methylation-altered DNA sequence or CpG island); TaqMan® probes; optimized PCR buffers and deoxynucleotides; and Taq polymerase.

Quantitative MethyLight uses bisulfite to convert genomic DNA and the methylated sites are amplified using PCR with methylation independent primers. Detection probes specific for the methylated and unmethylated sites with two different fluorophores provides simultaneous quantitative measurement of the methylation. The Heavy Methyl technique begins with bisulfate conversion of DNA. Next specific blockers prevent the amplification of unmethylated DNA. Methylated genomic DNA does not bind the blockers and their sequences will be amplified. The amplified sequences are detected with a methylation specific probe. (Cottrell et al, 2004, Nuc. Acids Res. 32:e10, the contents of which is hereby incorporated by reference in its entirety).

The Ms-SNuPE technique is a quantitative method for assessing methylation differences at specific CpG sites based on bisulfite treatment of DNA, followed by single-nucleotide primer extension (Gonzalgo and Jones, 1997, Nucleic Acids Res. 25, 2529-2531). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. In some cases, small amounts of DNA are analyzed (e.g., microdissected pathology sections), and the method avoids utilization of restriction enzymes for determining the methylation status at CpG sites. Typical reagents (e.g., as is found in a typical Ms-SNuPE-based kit) for Ms-SNuPE analysis include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In another embodiment, the methylation status of selected CpG sites is determined using differential Binding-based Methylation Detection Methods. For identification of differentially methylated regions, one approach is to capture methylated DNA. This approach uses a protein, in which the methyl binding domain of MBD2 is fused to the Fc fragment of an antibody (MBD-FC) (Gebhard et al, 2006, Cancer Res. 66:6118-6128; and PCT Pub. No. WO 2006/056480 A2 (Relhi), the contents of which are hereby incorporated by reference in their entirety). This fusion protein has several advantages over conventional methylation specific antibodies. The MBD FC has a higher affinity to methylated DNA and it binds double stranded DNA. Most importantly the two proteins differ in the way they bind DNA. Methylation specific antibodies bind DNA stochastically, which means that only a binary answer can be obtained. The methyl binding domain of MBD-FC, on the other hand, binds DNA molecules regardless of their methylation status. The strength of this protein—DNA interaction is defined by the level of DNA methylation. After binding genomic DNA, eluate solutions of increasing salt concentrations can be used to fractionate non-methylated and methylated DNA allowing for a more controlled separation (Gebhard et al, 2006, Nucleic Acids Res. 34: e82). Consequently this method, called Methyl-CpG immunoprecipitation (MCIP), not only enriches, but also fractionates genomic DNA according to methylation level, which is particularly helpful when the unmethylated DNA fraction should be investigated as well.

In an alternative embodiment, a 5-methyl cytidine antibody to bind and precipitate methylated DNA. Antibodies are available from Abeam (Cambridge, Mass.), Diagenode (Sparta, N.J.) or Eurogentec (c/o AnaSpec, Fremont, Calif.). Once the methylated fragments have been separated they may be sequenced using microarray based techniques such as methylated CpG-island recovery assay (MIRA) or methylated DNA immunoprecipitation (MeDIP) (Pelizzola et al, 2008, Genome Res. 18, 1652-1659; O'Geen et al, 2006, BioTechniques 41(5), 577-580, Weber et al, 2005, Nat. Genet. 37, 853-862; Horak and Snyder, 2002, Methods Enzymol, 350, 469-83; Lieb, 2003, Methods Mol Biol, 224, 99-109). Another technique is methyl-CpG binding domain column/segregation of partly melted molecules (MBD/SPM, Shiraishi et al, 1999, Proc. Natl. Acad. Sci. USA 96(6):2913-2918).

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific.

For example, there are methyl-sensitive enzymes that preferentially or substantially cleave or digest at their DNA recognition sequence if it is non-methylated. Thus, an unmethylated DNA sample is cut into smaller fragments than a methylated DNA sample. Similarly, a hypermethylated DNA sample is not cleaved. In contrast, there are methyl-sensitive enzymes that cleave at their DNA recognition sequence only if it is methylated. Methyl-sensitive enzymes that digest unmethylated DNA suitable for use in methods of the technology include, but are not limited to, Hpall, Hhal, Maell, BstUI and Acil. In some instances, an enzyme that is used is Hpall that cuts only the unmethylated sequence CCGG. In other instances, another enzyme that is used is Hhal that cuts only the unmethylated sequence GCGC. Both enzymes are available from New England BioLabs®, Inc. Combinations of two or more methyl-sensitive enzymes that digest only unmethylated DNA are also used. Suitable enzymes that digest only methylated DNA include, but are not limited to, Dpnl, which only cuts at fully methylated 5'-GATC sequences, and McrBC, an endonuclease, which cuts DNA containing modified cytosines (5-methylcytosine or 5-hydroxymethylcytosine or N4-methylcytosine) and cuts at recognition site 5' . . . PumC(N4o-3ooo) PumC . . . 3' (New England BioLabs, Inc., Beverly, Mass.). Cleavage methods and procedures for selected restriction enzymes for cutting DNA at specific sites are well known to the skilled artisan. For example, many suppliers of restriction enzymes provide information on conditions and types of DNA sequences cut by specific restriction enzymes, including New England BioLabs, Pro-Mega Biochems, Boehringer-Mannheim, and the like. Sambrook et al. (See Sambrook et al. Molecular Biology: A Laboratory Approach, Cold Spring Harbor, N.Y. 1989) provide a general description of methods for using restriction enzymes and other enzymes.

In some instances, a methylation-dependent restriction enzyme is a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., Dpnl) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, Bisl, Glal and Dpnl. One of skill in the art will appreciate that any methylation-dependent restriction enzyme, including homologs and orthologs of the restriction enzymes described herein, is also suitable for use with one or more methods described herein.

In some cases, a methylation-sensitive restriction enzyme is a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al, 22(17) NUCLEIC ACIDS RES. 3640-59 (1994). Suitable methylation-sensitive restriction enzymes that do not cleave DNA at or near their recognition sequence when a cytosine within the recognition sequence is methylated at position C5 include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinPl I, HinC II, Hpa II, Hpy99 I, HpyCH4 IV, Kas I, Mbo I, Mlu I, MapAl I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position N6 include, e.g., Mbo I. One of skill in the art will appreciate that any methylation-sensitive restriction enzyme, including homologs and orthologs of the restriction enzymes described herein, is also suitable for use with one or more of the methods described herein. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

In alternative embodiments, adaptors are optionally added to the ends of the randomly fragmented DNA, the DNA is then digested with a methylation-dependent or methylation-sensitive restriction enzyme, and intact DNA is subsequently amplified using primers that hybridize to the adaptor sequences. In this case, a second step is performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The methylated CpG island amplification (MCA) technique is a method that can be used to screen for altered methylation patterns in genomic DNA, and to isolate specific sequences associated with these changes (Toyota et al, 1999, Cancer Res. 59, 2307-2312, U.S. Pat. No. 7,700,324 (Issa et al), the contents of which are hereby incorporated by reference in their entirety). Briefly, restriction enzymes with different sensitivities to cytosine methylation in their recognition sites are used to digest genomic DNAs from primary tumors, cell lines, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

Additional methylation detection methods include those methods described in, e.g., U.S. Pat. Nos. 7,553,627; 6,331,393; U.S. patent Ser. No. 12/476,981; U.S. Patent Publication No. 2005/0069879; Rein, et al, 26(10) NUCLEIC ACIDS RES. 2255-64 (1998); and Olek et al, 17(3) NAT. GENET. 275-6 (1997).

In another embodiment, the methylation status of selected CpG sites is determined using Methylation-Sensitive High Resolution Melting (HRM). Recently, Wojdacz et al. reported methylation-sensitive high resolution melting as a technique to assess methylation. (Wojdacz and Dobrovic, 2007, Nuc. Acids Res. 35(6) e41; Wojdacz et al. 2008, Nat. Prot. 3(12) 1903-1908; Balic et al, 2009 J. Mol. Diagn. 11 102-108; and US Pat. Pub. No. 2009/0155791 (Wojdacz et al), the contents of which are hereby incorporated by reference in their entirety). A variety of commercially available real time PCR machines have HRM systems including the Roche LightCycler480, Corbett Research RotorGene6000, and the Applied Biosystems 7500. HRM may also be combined with other amplification techniques such as pyrosequencing as described by Candiloro et al. (Candiloro et al, 2011, Epigenetics 6(4) 500-507).

In another embodiment, the methylation status of selected CpG locus is determined using a primer extension assay, including an optimized PCR amplification reaction that produces amplified targets for analysis using mass spectrometry. The assay can also be done in multiplex. Mass spectrometry is a particularly effective method for the detection of polynucleotides associated with the differentially methylated regulatory elements. The presence of the polynucleotide sequence is verified by comparing the mass of the detected signal with the expected mass of the polynucleotide of interest. The relative signal strength, e.g., mass peak on a spectra, for a particular polynucleotide sequence indicates the relative population of a specific allele, thus enabling calculation of the allele ratio directly from the data. This method is described in detail in PCT Pub. No. WO 2005/012578A1 (Beaulieu et al), which is hereby incorporated by reference in its entirety. For methylation analysis, the assay can be adopted to detect bisulfite introduced methylation dependent C to T sequence changes. These methods are particularly useful for performing multiplexed amplification reactions and multiplexed primer extension reactions (e.g., multiplexed homogeneous primer mass extension (hME)

assays) in a single well to further increase the throughput and reduce the cost per reaction for primer extension reactions.

Other methods for DNA methylation analysis include restriction landmark genomic scanning (RLGS, Costello et al, 2002, Meth. Mol Biol, 200, 53-70), methylation-sensitive-representational difference analysis (MS-RDA, Ushijima and Yamashita, 2009, Methods Mol Biol 507, 1 17-130). Comprehensive high-throughput arrays for relative methylation (CHARM) techniques are described in WO 2009/021141 (Feinberg and Irizarry). The Roche® NimbleGen® microarrays including the Chromatin Immunoprecipitation-on-chip (ChIP-chip) or methylated DNA immunoprecipitation-on-chip (MeDIP-chip). These tools have been used for a variety of cancer applications including melanoma, liver cancer and lung cancer (Koga et al, 2009, Genome Res., 19, 1462-1470; Acevedo et al, 2008, Cancer Res., 68, 2641-2651; Rauch et al, 2008, Proc. Nat. Acad. Sci. USA, 105, 252-257). Others have reported bisulfate conversion, padlock probe hybridization, circularization, amplification and next generation or multiplexed sequencing for high throughput detection of methylation (Deng et al, 2009, Nat. Biotechnol 27, 353-360; Ball et al, 2009, Nat. Biotechnol 27, 361-368; U.S. Pat. No. 7,611,869 (Fan)). As an alternative to bisulfate oxidation, Bayeyt et al. have reported selective oxidants that oxidize 5-methylcytosine, without reacting with thymidine, which are followed by PCR or pyro sequencing (WO 2009/049916 (Bayeyt et al).

Pharmaceutical Formulations, Dosage Forms and Treatment Regimens

Another aspect of the present invention relates to formulations and routes of administration for pharmaceutical compositions comprising a nitrobenzamide compound. Such pharmaceutical compositions can be used to treat cancer in the methods described in detail above.

The compounds of Formula I may be provided as a prodrug and/or may be allowed to interconvert to a nitrosobenzamide form in vivo after administration. That is, either the nitrobenzamide form and/or the nitrosobenzamide form, or pharmaceutically acceptable salts may be used in developing a formulation for use in the present invention. Further, in some embodiments, the compound may be used in combination with one or more other compounds or in one or more other forms. For example a formulation may comprise both the nitrobenzamide compound and acid forms in particular proportions, depending on the relative potencies of each and the intended indication. The two forms may be formulated together, in the same dosage unit e.g. in one cream, suppository, tablet, capsule, or packet of powder to be dissolved in a beverage; or each form may be formulated in a separate unit, e.g., two creams, two suppositories, two tablets, two capsules, a tablet and a liquid for dissolving the tablet, a packet of powder and a liquid for dissolving the powder, etc.

In compositions comprising combinations of a nitrobenzamide compound and another active agent can be effective. The two compounds and/or forms of a compound may be formulated together, in the same dosage unit e.g. in one cream, suppository, tablet, capsule, or packet of powder to be dissolved in a beverage; or each form may be formulated in separate units, e.g., two creams, suppositories, tablets, two capsules, a tablet and a liquid for dissolving the tablet, a packet of powder and a liquid for dissolving the powder, etc.

The term "pharmaceutically acceptable salt" means those salts which retain the biological effectiveness and properties of the compounds used in the present invention, and which are not biologically or otherwise undesirable. For example, a pharmaceutically acceptable salt does not interfere with the beneficial effect of the compound of the invention in treating a cancer.

Typical salts are those of the inorganic ions, such as, for example, sodium, potassium, calcium and magnesium ions. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compounds used in the present invention contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexylamine, ethanolamine, diethanolamine and triethanolamine.

For oral administration, the compounds can be formulated readily by combining the active compound(s) with pharmaceutically acceptable carriers well known in the art. Such carriers enable the compounds of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the compounds of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions may contain a nitrobenzamide compound with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In some embodiments, oils or non-aqueous solvents may be required to bring the compounds into solution, due to, for example, the presence of large lipophilic moieties. Alternatively, emulsions, suspensions, or other preparations, for example, liposomal preparations, may be used. With respect to liposomal preparations, any known methods for preparing liposomes for treatment of a condition may be used. See, for example, Bangham et al., J. Mol. Biol, 23: 238-252 (1965) and Szoka et al., Proc. Natl Acad. Sci 75: 4194-4198 (1978), incorporated herein by reference. Ligands may also be attached to the liposomes to direct these compositions to particular sites of action. Compounds of this invention may also be integrated into foodstuffs, e.g, cream cheese, butter, salad dressing, or ice cream to facilitate solubilization, administration, and/or compliance in certain patient populations.

Pharmaceutical preparations for oral use may be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The compounds may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

For injection, the inhibitors of the present invention may be formulated in aqueous solutions, preferably in physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton Pa. These compounds may also be formulated for transmucosal administration, buccal administration, for administration by inhalation, for parental administration, for transdermal administration, and rectal administration.

In addition to the formulations described previously, the compounds may also be formulated as a depot preparation. Such long acting formulations may be administered by implantation or transcutaneous delivery (for example subcutaneously or intramuscularly), intramuscular injection or use of a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

As described elsewhere herein, in some instances 4-iodo-3-nitrobenzamide or a salt, metabolite or prodrug thereof is administered from about 5 mg/kg to about 200 mg/kg, from about 5 mg/kg to about 150 mg/kg, from about 5 mg/kg to about 100 mg/kg, or from about 5 mg/kg to about 60 mg/kg. In other instances, 4-iodo-3-nitrobenzamide or a salt, metabolite or prodrug thereof is administered at about 5 mg/kg, about 6 mg/kg, about 7 mg/kg, about 8 mg/kg, about 8.5 mg/kg, about 8.6 mg/kg, about 9 mg/kg, about 10 mg/kg, about 15 mg/kg, about 20 mg/kg, about 25 mg/kg, about 30 mg/kg, about 40 mg/kg, about 50 mg/kg, or about 60 mg/kg.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, e.g., the specific agent being administered, the route of administration, and the subject or host being treated. The desired dose may conveniently be presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. Compounds exhibiting high therapeutic indices are preferred. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include iniparib, optionally in a composition or in combination with temozolomide. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "first-line treatment" refers to a primary treatment for a subject with a cancer. In some instances, the cancer is a primary cancer. In other instances, the cancer is a metastatic or recurrent cancer. In some cases, the first-line treatment comprises chemotherapy. In other cases, the first-line treatment comprises radiation therapy. A skilled artisan would readily understand that different first-line treatments may be applicable to different type of cancers.

EXAMPLES

These examples are provided for illustrative purposes only and not to limit the scope of the claims provided herein.

Example 1—Phase I Clinical Trial—Glioblastoma Multiforme (GBM)

The Iniparib phase 1 GBM study was a multicenter study. It was a single arm, multi dose, dose escalating trial in newly diagnosed GBM patients. The total number of patients was 43, with about 5 patients per cohort. Patients who tolerated radiation (XRT) and temozolomide (TMZ) were recruited. Inclusion criteria included completion of XRT and TMZ without grade 3 or 4 toxicity and labs within acceptable range within 6 weeks of completing XRT. The end points included safety, maximum tolerated dose (MTD), and signal of activity.

The patients were separated into two study groups with the following treatment schema (also see FIG. 1).

Study Group 1 Treatment Cycles 4 Weeks Each (N=23)
Cycle 1
Days 1-5: TMZ 150 mg/m$^2$
Weeks 1-4: BSI-201, starting dose 5.1 mg/kg
Cycle 2
Days 1-5: TMZ 200 mg/m$^2$
Weeks 1-4: BSI-201, starting dose 5.1 mg/kg
MRI performed after every odd cycle (every 8 weeks) until progression.
Study Group 2 Treatment Cycles 10 Weeks Each (N=20)
Weeks 1-6: TMZ Daily 75 mg/m$^2$
Weeks 1-6: BSI-201, starting dose 5.1 mg/kg Weeks 7-10: Rest, no treatment
MRI performed after every cycle (every 10 weeks) until progression.

Continuous Reassessment Method (CRM) was used to determine dose escalation. PK was drawn at cycle 1, 2, 3 and off treatment. PD via PBMCs was drawn at cycle 1, 2, 3 and off treatment. No cytochrome P450-inducing anticonvulsants. However, Gliadel was permitted.

In Adjuvant Phase:
Group 1: TMZ (150-200 mg/m$^2$ given 5 days/month×6 cycles)—standard dose with BSI-201 starting at 5.1 mg/kg.
Group 2: TMZ (75 mg/m$^2$ daily 42 days on 30 days off×3 cycles)—metronomic dose with BSI-201 starting at 5.1 mg/kg.

Using modified continual reassessment method, MTD was defined for metronomic and standard dose TMZ. 6 dose levels were tested (lowest 5.1 mg/kg-highest 9.5 mg/kg IV 2×/wk). At 8.6 mg/kg (17.2 mg/kg/week), 1/9 patients had a DLT. The DLTs across both groups were: rash (1), hypersensitivity reaction (1), fatigue (1) and a thromboembolic event (1). Additional grade 3 toxicities were neutropenia, lymphopenia, nausea, and elevated AST. Phase 2 dose defined as 8 mg/kg IV 2×/wk with standard TMZ and 8.6 mg/kg IV 2×/wk with metronomic TMZ.

Table 1 illustrates the pharmacokinetics of iniparib. Data are presented as the geometric mean±SD for peak plasma concentrations ($C_{max}$) and the arithmetic average±SD for the metabolite/iniparib concentration ratio as expressed as a percentage. Dosing is IV 2×/week continuous. IABM and IABA are the two major metabolites of iniparib in plasma.

| Dose (mg/kg) | No. of Patients | No. of samples | $C_{max}$ (ng/mL) | | | Metabolite/iniparib (%) | |
|---|---|---|---|---|---|---|---|
| | | | Iniparib | IABM | IABA | IABM | IABA |
| 5.1 | 8 | 20 | 642 ± 315 | 5.7 ± 4.1 | 16.6 ± 5.2 | 1.1 ± 0.6 | 3.0 ± 2.0 |
| 6.1 | 5 | 11 | 928 ± 397 | 7.2 ± 1.8 | 14.9 ± 8.3 | 0.9 ± 0.6 | 2.0 ± 1.5 |
| 6.8 | 7 | 18 | 1,019 ± 463 | 8.4 ± 3.7 | 19.9 ± 6.6 | 1.1 ± 0.9 | 2.4 ± 1.4 |
| 8.0 | 4 | 5 | 3,687 ± 1,464 | 10.3 ± 2.9 | 14.5 ± 15.0 | 0.3 ± 0.1 | 0.7 ± 0.7 |
| 8.6 | 5 | 18 | 1,517 ± 987 | 9.7 ± 2.4 | 31.5 ± 10.4 | 0.8 ± 0.6 | 2.5 ± 1.4 |
| 9.5 | 4 | 7 | 2,139 ± 2,133 | 13.6 ± 5.3 | 19.8 ± 14.0 | 0.8 ± 0.6 | 2.0 ± 2.0 |

Table 2 illustrates the toxicity of iniparib. Grade 3-4 adverse events are shown with relationship of possible, or probable, or definite to iniparib.

| Adverse Event | Group I N = 23 No. (% of pts) | Group II N = 20 No. (% of pts) | Total N = 43 No. (% of pts) |
|---|---|---|---|
| Allergic reaction | 1 (4) | | 1 (2) |
| Alanine | | 6 (30) | 6 (14) |
| Anemia | 13 (57) | 11 (55) | 24 (56) |
| Constipation | 9 (39) | 7 (35) | 16 (37) |
| Dizziness | 5 (22) | | 5 (12) |
| Fatigue | 15 (65) | 13 (65) | 28 (65) |
| Nausea | 9 (39) | 9 (45) | 18 (42) |
| Rash maculo-papular | 5 (22) | | 5 (12) |
| Thromboembolic event | | 1 (5) | 1 (2) |
| Lymphocyte count decreased | | 6 (30) | 6 (14) |
| Platelet decreased | 15 (65) | 6 (30) | 21 (49) |
| White counts decreased | 11 (48) | 11 (55) | 22 (51) |

Example 2—Phase II Clinical Trial—Glioblastoma Multiforme (GBM)

The primary objective of the Phase II study was to estimate the overall survival for adult patients with newly diagnosed glioblastoma multiforme (GBM) treated with BSI-201 (iniparib) at the MTDs during RT with concurrent and adjuvant TMZ. The secondary objective was to estimate the frequency of toxicity associated with this treatment regimen. 76 patients were recruited for this study. Corollary studies included PARP-1 expression in resected GBM and MGMT status in resected GBM.

Safety Run-In:

BSI-201 at one dose less than the MTD from Group 2 with TMX 75 mg/m²+XRT (3 patients), then BSI-201 at Group 2 MTD with TMX 75 mg/m²+XRT (3 patients) to ensure safety of triple therapy.

Figure 2:
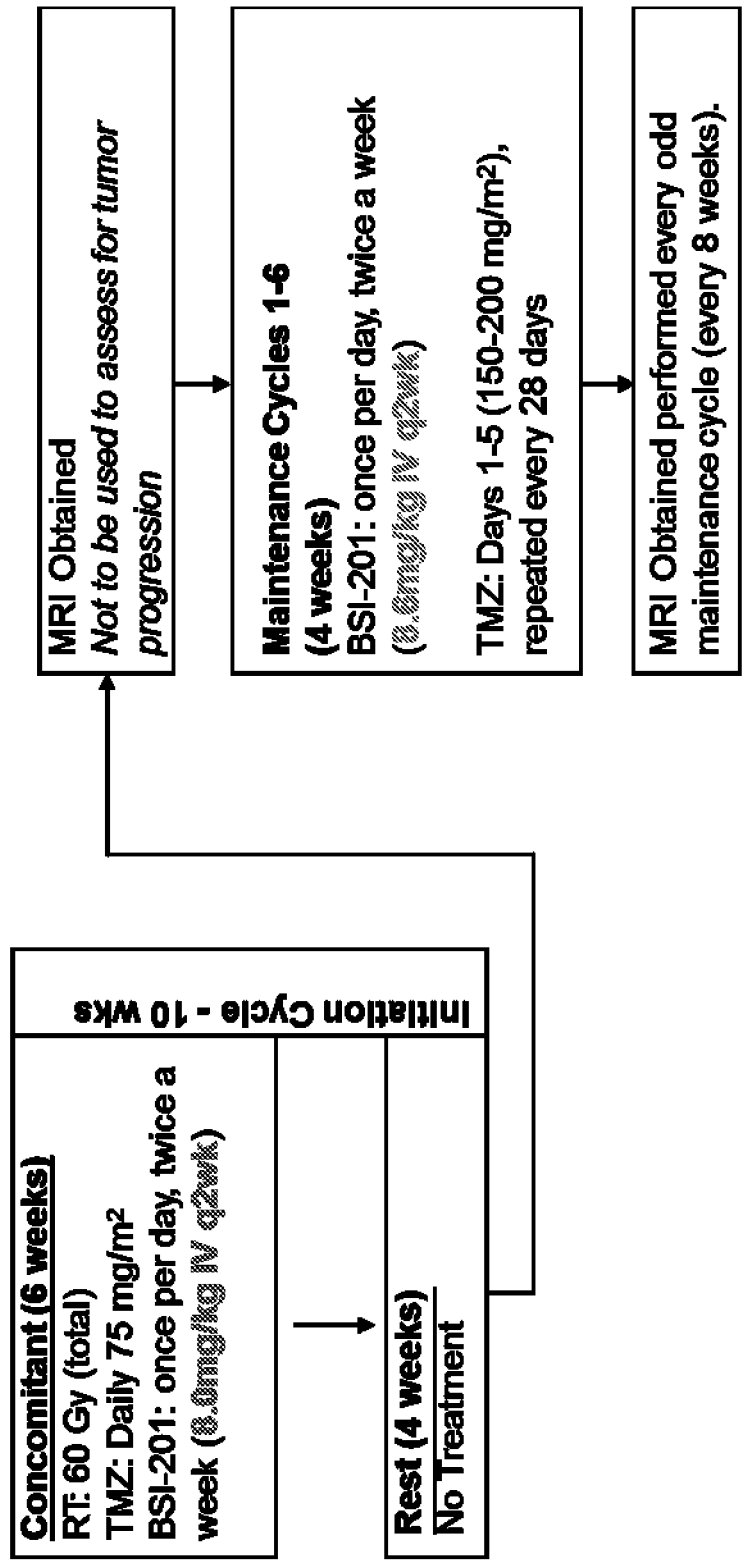
FIG. 2 illustrates an exemplary Phase II treatment schema.

The following treatment schema (also see FIG. 2).
Concomitant (6 weeks)
RT: 60 Gy (total) TMZ: Daily 75 mg/m²
BSI-201: once per day, twice a week (8.0 mg/kg IV q2 wk)
Rest (4 weeks) with no treatment.
Maintenance Cycles 1-6 (4 weeks)
BSI-201: once per day, twice a week (8.6 mg/kg IV q2 wk)
TMZ: Days 1-5 (150-200 mg/m²), repeated every 28 days For assessing the efficacy of the treatment in terms of overall survival, the overall failure rate were estimated and compared to the failure rate of 0.6 per-person year of follow-up regarding the Phase III trial done by Stupp et al. in the same patient population treated with RT plus concomitant and adjuvant temozolomide.

The primary endpoint was death due to all causes. The survival time is defined from time of histological diagnosis to death occurrence. The overall failure rate was expressed as hazard of failure per person-year of follow-up. The total patient population for this part of the study was defined as all patients who have met the eligibility criteria, not met ineligibility criteria, and signed patient informed consent.

Some of the patients received a corticosteroid (e.g., dexamethasone) during the trial period.

It was assumed that the patients in the study had an overall failure rate of 0.45 per person-year of planned follow-up. It is approximately 25% reduction in hazard rate compared to a hazard rate of 0.6 in the Phase III trial done by Stupp et al. With a total of 55 events among 76 patients, the study yield 80% power to detect an observed hazard ratio of 0.75 (0.45 vs. 0.6) at an alpha level of 0.1(one-sided) to be statistically significant. It yield above 90% power to detect a 30% reduction in hazard rate with observed hazard ratio of 0.7 (0.42 vs. 0.6) at an alpha level of 0.1 to be significant. The overall failure rate was estimated by dividing the number of events (deaths) by the total exposure time in the study cohort along with 95% confidence intervals. Survival probability and median time of survival was calculated using Kaplan-Meier method.

Table 3 illustrates the demographics of the patients.

| | All Patients (N = 81) |
|---|---|
| Age: Median (Range) | 58 (27-80.9) |
| Gender: No. Male (%) | 51 (63) |
| RACE: | |
| White: No. (%) | 77 (95) |
| Ethnic Group: | |
| Hispanic or Latino: No. (%) | 1 (1) |
| Not Hispanic or Latino: No. (%) | 74 (91) |
| Unknown: No. (%) | 6 (7) |

-continued

| | All Patients (N = 81) |
|---|---|
| Anticonvulsant: | |
| Yes: No. (%) | 64 (79) |
| No: No. (%) | 17 (21) |
| KPS: | |
| 100: No. (%) | 9 (11) |
| 90: No. (%) | 40 (49) |
| 80: No. (%) | 22 (27) |
| 70: No. (%) | 8 (10) |
| 60: No (%) | 2 (2) |
| Mini Mental Score: Median (Range) | 29 (22-30) |
| Diagnosis: | |
| Glioblastoma Multiforme: No. (%) | 80 (99) |
| Gliosarcoma: No. (%) | 1 (1) |
| Surgical Procedure | |
| Craniotomy: No. (%) | 77 (95) |
| Biopsy: No. (%) | 4 (5) |

Table 4 illustrates toxicity and tolerability.

| Adverse Events: N (%) | Grade 3 | Grade 4 | Total | Stupp et al, 2005 |
|---|---|---|---|---|
| Acute kidney injury | 1 (1) | | 1 (1) | |
| Alanine aminotransferase increased | | 1 (1) | 1 (1) | |
| Anemia | 2 (2) | | 2 (2) | |
| Aspartate aminotransferase increased | | 1 (1) | 1 (1) | |
| Atrial fibrillation | 1 (1) | | 1 (1) | |
| Bronchial infection | 1 (1) | | 1 (1) | |
| Cognitive disturbance | 1 (1) | | 1 (1) | |
| Confusion | 1 (1) | | 1 (1) | |
| Dehydration | 1 (1) | | 1 (1) | |
| Dizziness | 1 (1) | | 1 (1) | |
| Dysphasia | 1 (1) | | 1 (1) | |
| Fatigue | 4 (5) | | 4 (5) | |
| Flushing | | 1 (1) | 1 (1) | |
| Generalized muscle weakness | 2 (2) | | 2 (2) | |
| Headache | 1 (1) | | 1 (1) | |
| Hyperkalemia | 1 (1) | | 1 (1) | |
| Hypertension | | 1 (1) | 1 (1) | |
| Hypokalemia | 1 (1) | | 1 (1) | |
| Hypotension | 1 (1) | | 1 (1) | |
| Hypoxia | 1 (1) | | 1 (1) | |
| Lymphocyte count decreased | 4 (5) | | 4 (5) | |
| Nausea | 2 (2) | | 2 (2) | |
| Neutrophil Count Decreased | 3 (4) | 5 (6) | 8 (10) | 7% |
| Platelet Count Decreased | 4 (5) | 11 (13) | 15 (18) | 12% |
| Rash maculo-papular | 3 (4) | | 3 (4) | |
| Skin and subcutaneous tissue disorders | 1 (1) | | 1 (1) | |
| Vomiting | 1 (1) | | 1 (1) | |
| White Blood Cell Decreased | 5 (6) | 3 (4) | 8 (10) | 7% |

Figure 3:
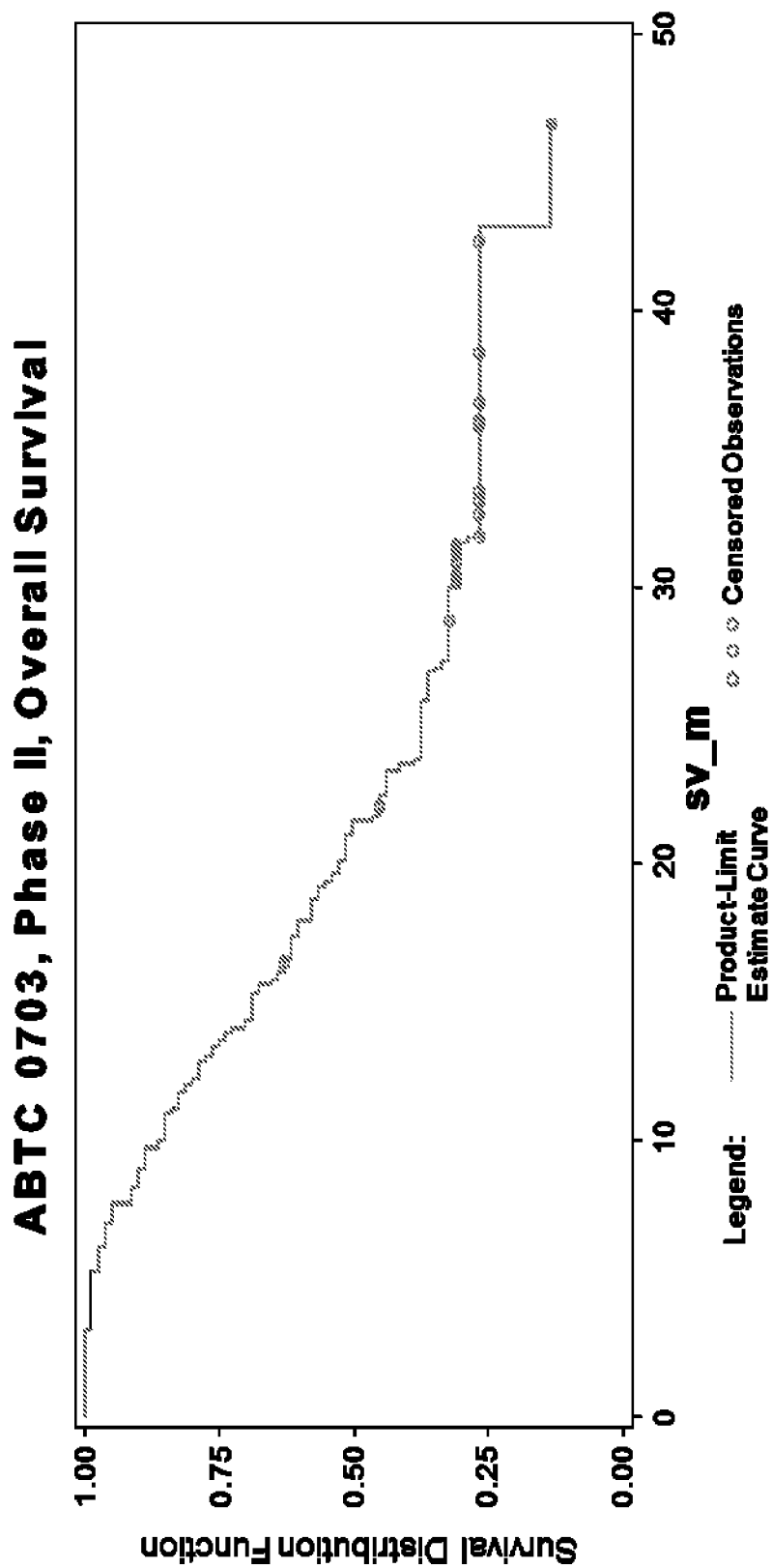
FIG. 3 shows an overall survival analysis from the Phase II trial described herein.

FIG. 3 and Table 5 show the overall survival analysis. Hazard rate of death at 0.6 was the null hypothesis to against an alternative hypothesis of 0.42 by the trial design. The treatment has achieved the target therapeutic effect which yielded a hazard rate of 0.403 per person year of follow-up.

TABLE 5

| Trial | Median Overall Survival Months, (95% CI) | Hazard Rate (95% CI) (per person year of follow-up) |
|---|---|---|
| ABTC0703 n = 76 | 21.6 (16.1-23.7) | 0.403 (0.308-0.526) |
| EORTC Stupp, 2005* n = 287 | 14.6 | 0.6 (*conversion) |
| RTOG 0525, 2013 STD arm, n = 411* | 16.6 | 0.501 (*conversion) |
| RTOG 0525, 2013 DD arm, n = 422* | 14.9 | 0.558 (*conversion) |

Figure 4:
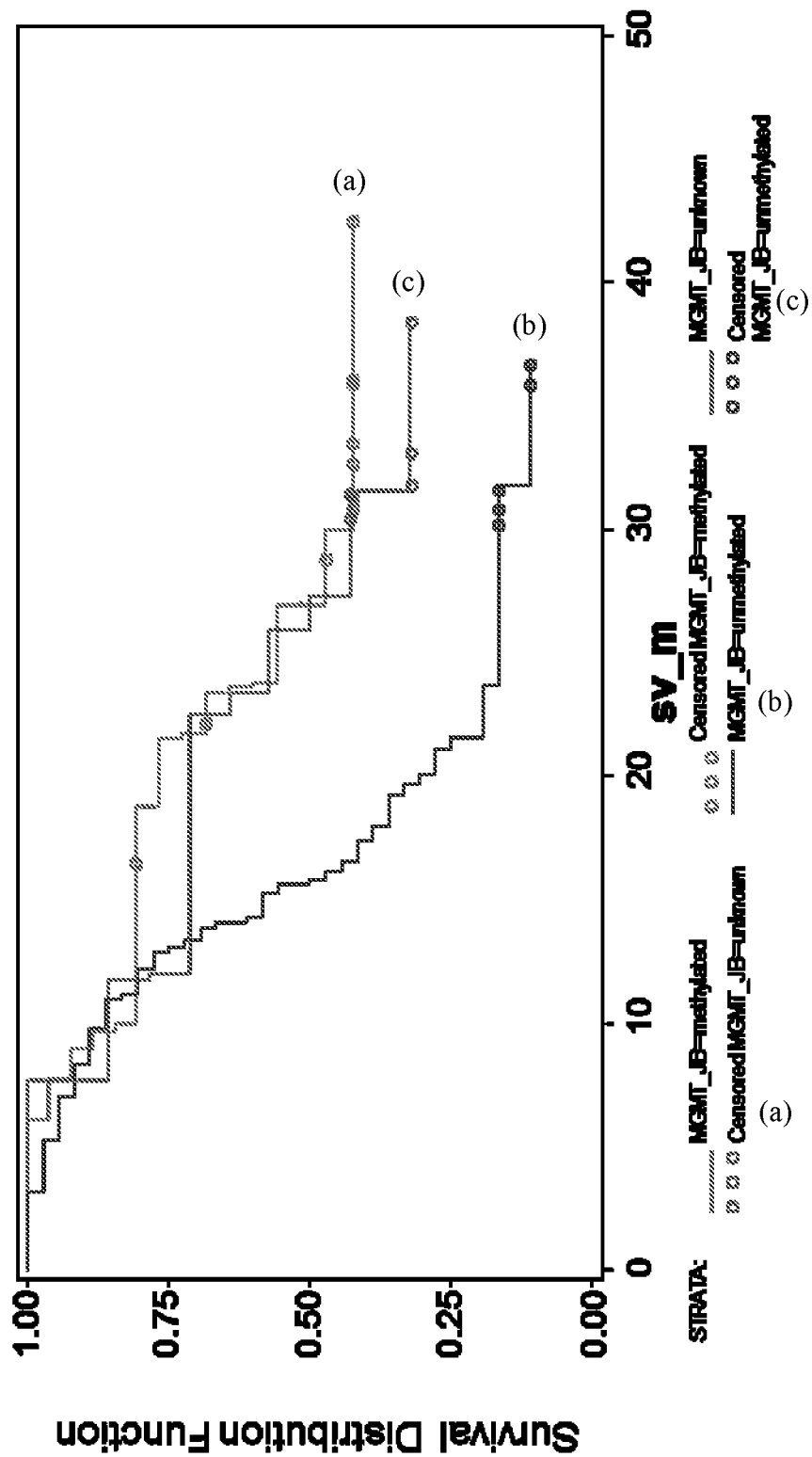
FIG. 4 illustrates an overall survival by MGMT status from the Phase II trial described herein.

FIG. 4 and Table 6 illustrate overall survival by MGMT status.

TABLE 6

| Trial | Median Overall Survival Months, (95% CI) | Median Overall Survival Months, (95% CI) |
|---|---|---|
| MGMT | mOS, MGMT methylated | mOS, MGMT unmethylated |
| ABTC0703 | 27 (n = 29) | 15.8 (n = 37) |
| EORTC Stupp, 2005 | 21.7 (n = 46) | 12.7 (n = 60) |
| RTOG 0525 | 21.4 (n = 122) sTMZ | 14.6 (n = 254) sTMZ |
| | 20.2 (n = 123) ddTMZ | 13.3 (n = 263) ddTMZ |

Figure 5:
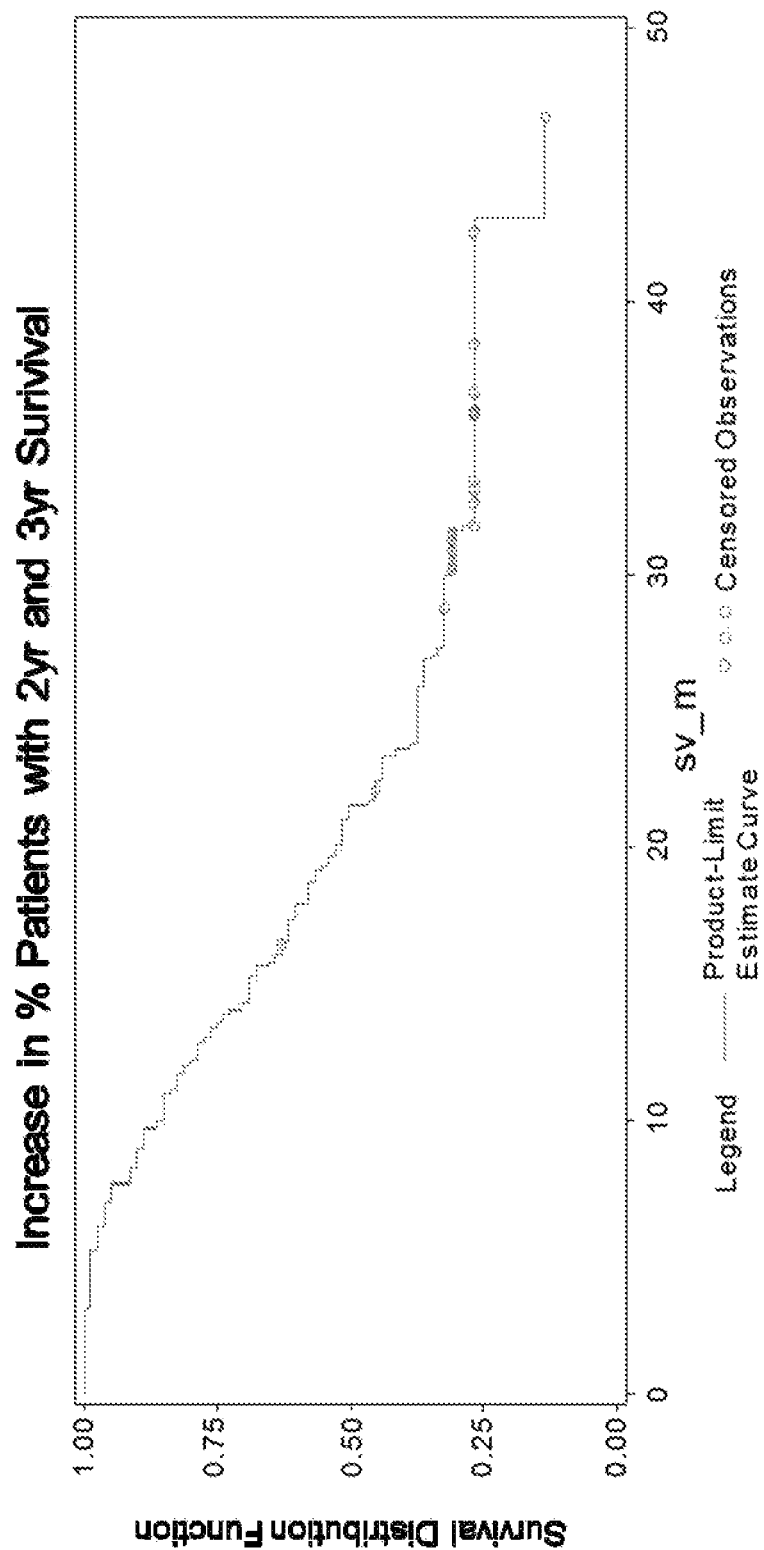
FIG. 5 illustrates an increase in the percentage of patients with 2 year survival and 3 year survival.

FIG. 5 and Table 7 illustrate an increase in the percentage of patients with 2 year survival and 3 year survival.

TABLE 7

| Trial | 2 Year Survival (% patients) | 3 Year Survival (% patients) |
|---|---|---|
| Iniparib Phase 2 N = 76 | 42.1 | 23.7 |
| EORTC Stupp, 2005 n = 287 | 27.2 | 16.0 |

Iniparib well tolerated at doses of 16 mg/kg weekly with radiation and TMZ and 17.2 mg/kg weekly with adjuvant TMZ Single arm phase 2 met efficacy endpoint with at least a 25% reduced HR versus Stupp et al 2005

Also improved over RTOG 0525 (2013), but extrapolated and not pre-planned analysis.

Example 3—Iniparib is a Cytotoxic Anti-Tumor Prodrug Bioactivated by TrxR1/2

Materials

Cell line is purchased from the ATCC cell biology collection. Cell culture reagents are purchased from LifeTechnologies. All regular chemicals or reagents are obtained from Sigma-Aldrich Chemicals, unless otherwise specified.

Cell Culture

HTB-16 cells are cultured in DMEM medium supplemented either with 10% fetal bovine serum, 2 mM glutamine, 1 mM sodium pyruvate and 10 μg/ml ciprofloxacine (Euromedex) in a humidified 5% CO2 atmosphere at 37° C.

Fluorescence Microscopy.

HTB-16 cells are platted on polylysine D coated thin glass bottom microscope chambers (Ibidi). After 24 h of culture cells are first pre-incubated with BSO at 1 mM for 18 h and then treated with 100 µM iniparib-Biotin or its vehicle (DMSO 1%) for 30 min. For subcellular localization experiments mitochondria are stained with 100 nM Mitotracker Red CMX (Molecular probes) added for 10 min. This stain is performed before fixation (Paraformaldehyde 3.7% in PBS pH 7.4). Biotin is developed, after Triton X100 (0.3% in PBS, 15 min) permeabilization and saturation (1% BSA+ 1% gelatin in PBS: saturation buffer), with Alexa-488 streptavidin (Molecular Probes) conjugate (1 µg/ml in saturation buffer). Nuclei are stained with Hoechst (Molecular Probes) and samples mounted in antifading solution (Ibidi).

Cells are imaged with a PLAN NeoFluar 40× (NA 1.3) or 100×, (NA 1.46) oil objectives on a LSM510 (Zeiss) confocal microscope. Laser lines, filters and dichroic mirrors are selected for maximal separation of the green (Ex./Em. 488/530 nm) and the red fluorescence (Ex./Em. 543/LP 585 nm). Nuclei are observed (Ex./Em. 405/460 nm). For co-localization stacks of images separated by 400 nm along z-axis are acquired. Post-capture processing is done using LSM510 software, stacks of confocal images were deconvoluted using the ImageJ software.

TrxR Activity

TrxR activity is measured by the reduction of 5, 5'-dithiobis-2-nitrobenzoic acid (DTNB) according to the manufacturer's instructions (TrxR assay kit, Sigma). Briefly, all incubations are performed at 37° C. in 96-well microplates in 0.1 M potassium phosphate (pH 7.4), 10 mM EDTA and 240 µM NADPH. TrxR activity is measured by recording the initial increase in A412 during the first 10 min upon addition of 3 mM DTNB with a scanning multiwell spectrophotometer (Molecular devices). Endogenous TrxR activity is determined using clarified octyl-glucoside cell lysates (50 µg proteins). Initial velocities are derived from linear regression analyses and then plotted in double reciprocal plots to obtain the half time of TrxR inhibition using an one phase exponential decay analysis (Prism, GraphPad software).

Trx Western Blot Analysis

A modification of a standard Western blot allows quantification of the redox state of specific proteins by separation of reduced and oxidized forms by gel electrophoresis and detection of both forms with an antibody to an epitope that does not undergo oxidation-reduction (FIG. 6). Quantification is obtained directly from the relative intensities of the different bands. Two forms of the redox Western blot are developed, separating on the basis of differing charge (thiols are modified with a charged alkylating reagent) or mass (thiols are modified with a high-mass alkylating reagent). Redox analysis of the mitochondrial compartment is performed using a redox Western blot analysis of thioredoxin-2 (Trx2). Trx2 is exclusively found in mitochondria, so an analysis of a cell or tissue extract provides specific information on redox in the mitochondria without fractionation. Analysis is performed following derivatization with AMS. Trx2 contains two cysteine residues, and the addition of two molecules of AMS increases the mass by approximately 1000 Da. Oxidized and AMS derivatized forms are separated by non-reducing SDS polyacrylamide gel electrophoresis and detected by immunoblotting.

ROS Production and Video-Microscopy.

HTB-16 cells are platted in Ibidi® treated chambers. After 24 h of culture cells are first pre-incubated with BSO at 1 mM for 18 h and then treated with 100 µM iniparib or its vehicle (DMSO 1%) for 4 h. For ROS and nuclei detection, cells are respectively loaded with 5 M CellROXOrange® (Molecular Probes) and 5 µM of DRAQ5® (Cell Signaling technology) in fresh media for 30 min.

Image acquisition is performed after washes with an Axiovert 200 Zeiss (Carl Zeiss Jena Germany) microscope equipped with a 40× C-Apochromat objective (N.A.=0.95). CellROXOrange® and DRAQ5® fluorescences are respectively excited with a LED light source (595 and 646 nm) and emitted light are collected at 565 and 681 nm. For quantification ImageJ software is used. Data is presented as Integrated Intensities/nuclei.

Clinical Trial Panel.

Clinical trials are conducted to test the efficacy of iniparib for patients with glioblastoma. Formalin-fixed, paraffin-embedded (FFPE) archival samples from biopsy or surgery at original diagnosis of glioblastoma are profiled on the exon-based Affymetrix Hugene1.0ST microarrays using an RNA extraction protocol adapted to the short fragment lengths resulting from RNA degradation in FFPE samples.

Processing of Gene Expression Data.

The raw gene expression data in the form of individual Affymetrix CEL files are processed using MAS5 estimation. Quality control based on average array brightness further excludes outlier scans, and the remaining profiles are then normalized to each other using quantile normalization. Affymetrix probesets are mapped to genes, in a manner where multiple probesets mapping into the same gene are resolved by assigning the highest intensity to the corresponding gene. The data is then log 2-transformed, and standardized by mean-subtraction and division by the standard deviation across all samples, for each gene separately. Finally, the data matrix is subsetted to the intersection of the oxidative response set of genes with the set of genes represented on the Hugene1.0ST arrays.

Multivariate Cox Modeling, Based on Gene Expression Data and on an a Priori Oxidative Stress Gene Set.

A multivariate Cox model using supervised principal components is used to model progression free survival times regressed on gene expression data. The model is of the form $$\xi = \log\left(\frac{\lambda(t \mid x, z)}{\lambda_0(t)}\right) = \beta_0 z + \sum_{i=1}^{K} \tilde{\beta}_1 x_1 + z \cdot \sum_{i=1}^{K} \tilde{\gamma}_1 \tilde{x}_i \qquad \text{Eq. (1)}$$

where by definition ξ is the "log-hazard-ratio" for a given individual, λ(t|z, x) the hazard function (or risk per unit time) for that individual, with covariate vector (z, x), and PFS time t, λ0(t) the baseline hazard function (the hazard which applies to an individual with all covariates exactly equal to 0), and where z is a binary indicator of treatment arm, with z=0 for the control and z=1 for the iniparib treatment arm. The symbol x refers to the gene expression vector with p=a specific set of components (the subset of the oxidative stress gene set represented on the Affymetrix microarrays). Note that this model contains both direct and interaction terms, the coefficients $\tilde{\beta}_1$ accounting for the direct effects of gene expression (which might be called "prognostic" effects) and the coefficients $\tilde{\gamma}_1$ accounting for gene expression x treatment-arm effects ("predictive" effects). The coefficient β0 accounts for overall, gene-expression independent, treatment-arm effects.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of treating glioblastoma in a subject in need thereof, comprising administering to the subject:
   about 8 mg/kg of 4-iodo-3-nitrobenzamide or a salt, metabolite or prodrug thereof;
   about 75 mg/m$^2$ of temozolomide; and
   radiation.

2. The method of claim 1, wherein about 60 Gy of radiation is administered to the subject over a course of about six weeks.

3. The method of claim 1, wherein the 4-iodo-3-nitrobenzamide or the salt, metabolite or prodrug thereof is administered to the subject once a day and twice a week.

4. The method of claim 1, wherein the 4-iodo-3-nitrobenzamide or the salt, metabolite or prodrug thereof is administered to the subject for about six weeks.

5. The method of claim 1, wherein temozolomide is administered to the subject daily.

6. The method of claim 1, wherein temozolomide is administered to the subject for about six weeks.

7. The method of claim 1, wherein upon completion of about six weeks of treatment with 4-iodo-3-nitrobenzamide or the salt, metabolite or prodrug thereof, temozolomide, and radiation, the subject receives a treatment break of about four weeks.

8. The method of claim 1, wherein the 4-iodo-3-nitrobenzamide or the salt, metabolite or prodrug thereof and the temozolomide is administered to the subject for about 1-6 cycles, wherein a single cycle is about 28 days.

9. The method of claim 8, wherein the temozolomide is administered to the subject on Days 1-5 of each cycle.

10. The method of claim 1, wherein the 4-iodo-3-nitrobenzamide or the salt, metabolite or prodrug thereof is formulated for parenteral administration, wherein the parenteral administration comprises intravenous, intra-arterial, intracranial, intracerebral, intracerebroventricular, or intrathecal administration.

11. The method of claim 1, wherein the 4-iodo-3-nitrobenzamide or the salt, metabolite or prodrug thereof is formulated as an injection or as an infusion.

12. The method of claim 1, wherein the glioblastoma is a primary glioblastoma or a secondary tumor.

13. The method of claim 1, wherein the subject has a grade III or grade IV glioblastoma.

* * * * *